(12) United States Patent  (10) Patent No.: US 8,144,394 B2
Uzawa  (45) Date of Patent: Mar. 27, 2012

(54) STEREOSCOPIC IMAGING OPTICAL SYSTEM

(75) Inventor: Tsutomu Uzawa, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 451 days.

(21) Appl. No.: 12/427,957

(22) Filed: Apr. 22, 2009

(65) Prior Publication Data

US 2009/0296206 A1  Dec. 3, 2009

(30) Foreign Application Priority Data

Apr. 23, 2008 (JP) ................................ 2008-112279

(51) Int. Cl.
*G02B 21/22* (2006.01)
*G02B 15/14* (2006.01)
*G02B 13/00* (2006.01)
(52) U.S. Cl. .................... 359/377; 359/687; 359/744
(58) Field of Classification Search .............. 359/376, 359/377, 378, 676, 687, 744
See application file for complete search history.

(56) References Cited

U.S. PATENT DOCUMENTS

| 6,327,079 | B1 | 12/2001 | Namii et al. |
| 7,085,045 | B2 | 8/2006 | Hanzawa et al. |
| 7,564,619 | B2 * | 7/2009 | Uzawa et al. ................. 359/377 |

* cited by examiner

*Primary Examiner* — Alessandro Amari

(74) *Attorney, Agent, or Firm* — Arnold International; Bruce Y. Arnold

(57) ABSTRACT

The invention provides a stereoscopic imaging optical system that has a total optical length short enough to be suitable for use in electron image microscopes. The stereoscopic imaging optical system comprises, in order from its object side, one objective lens DB and a plurality of zoom imaging optical systems ZI. Each zoom imaging optical system ZI comprises, in order from its object side, a positive first group G1, a negative second group G2, an aperture stop AS, a positive third group G3 and a positive fourth group G4. The second group moves for zooming on an optical axis, and the fourth group moves on the optical axis in association with the second group for correcting an image position fluctuation incidental to zooming. Various conditions are satisfied.

5 Claims, 35 Drawing Sheets

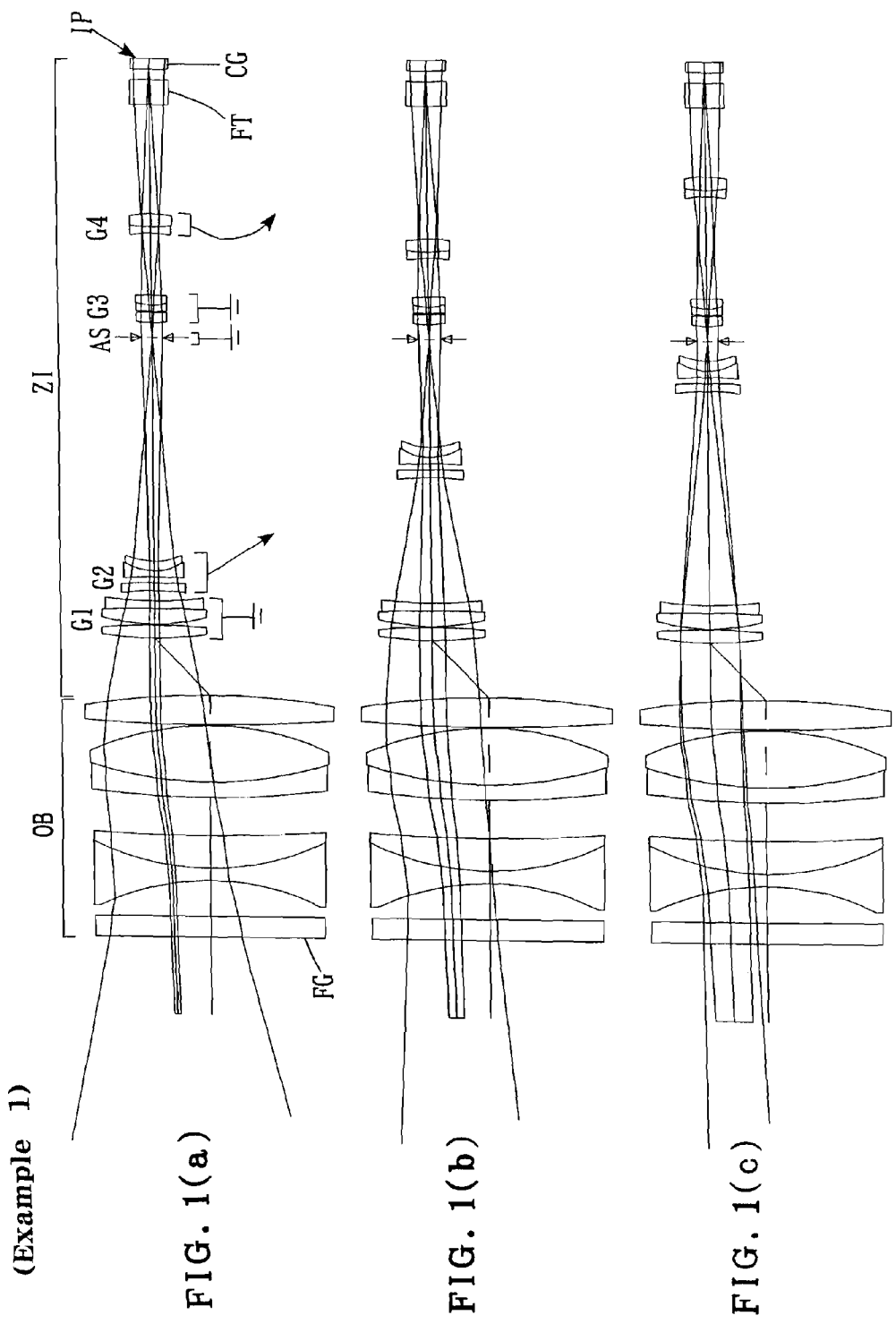

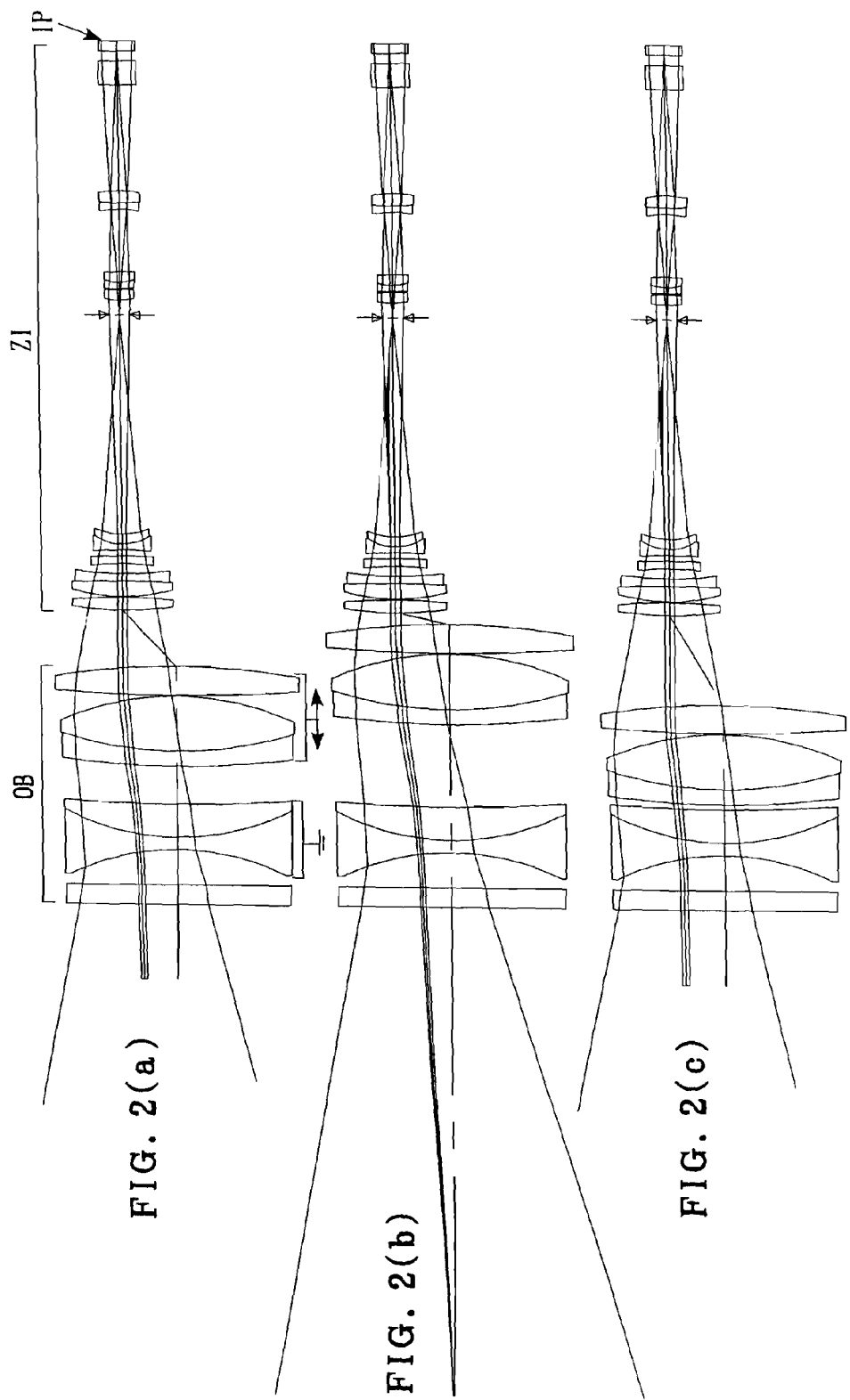

(Example 2)

(Example 3)

(Example 4)

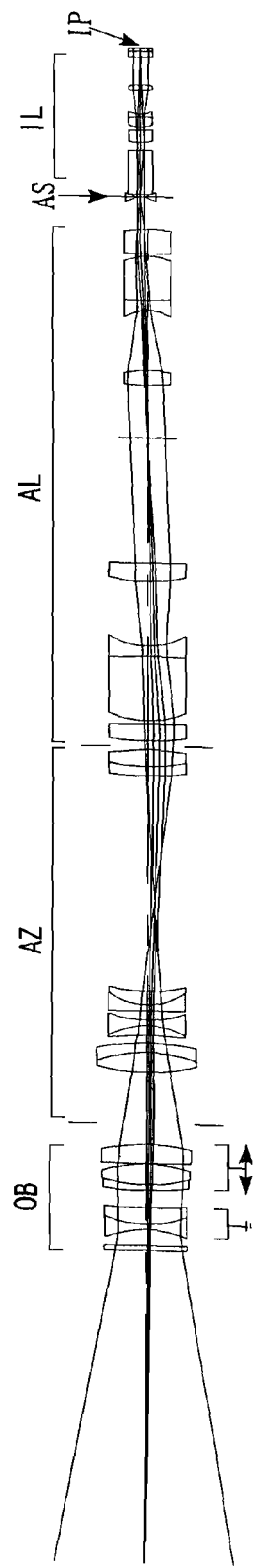
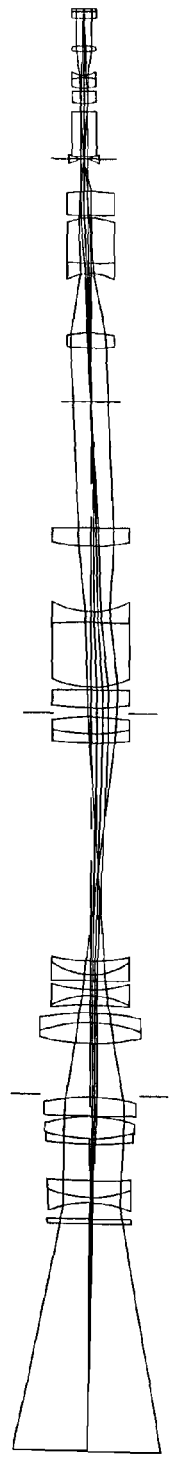
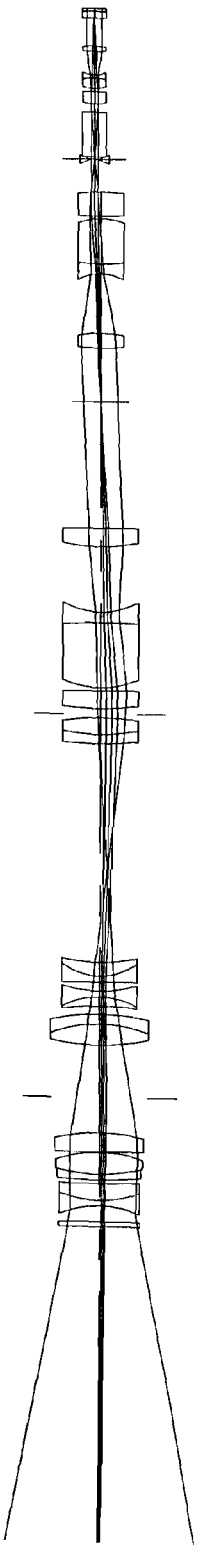
FIG. 6(a)
FIG. 6(b)
FIG. 6(c)
(Example 4)

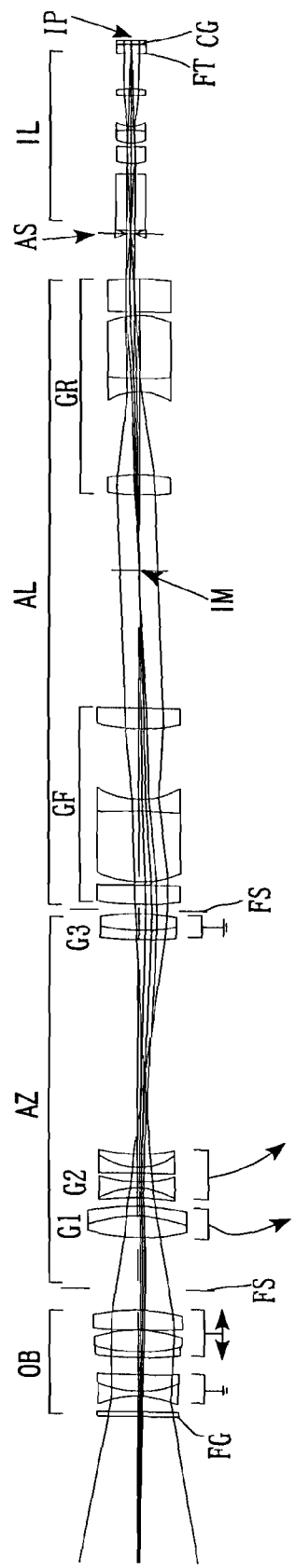
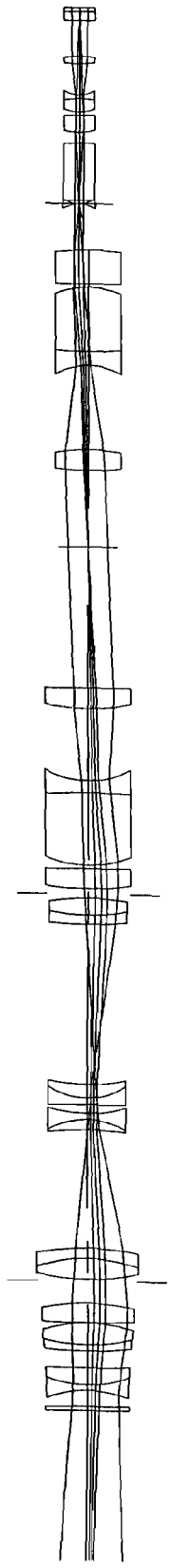
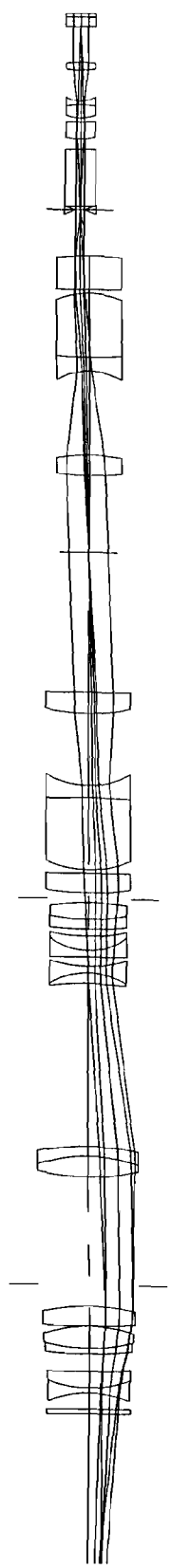
FIG. 7(a) (Example 5)
FIG. 7(b)
FIG. 7(c)

(Example 6)

(EXAMPLE 1)

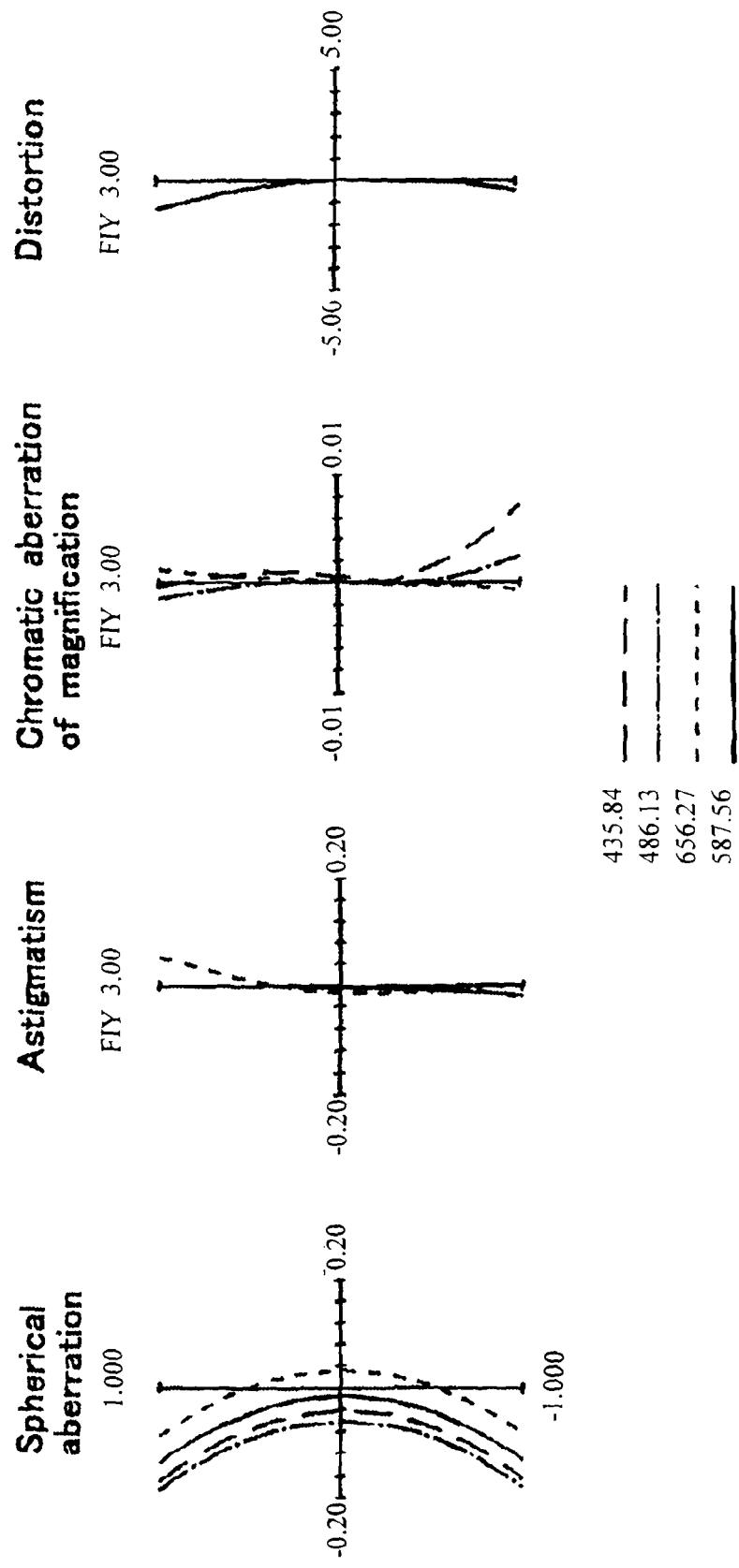

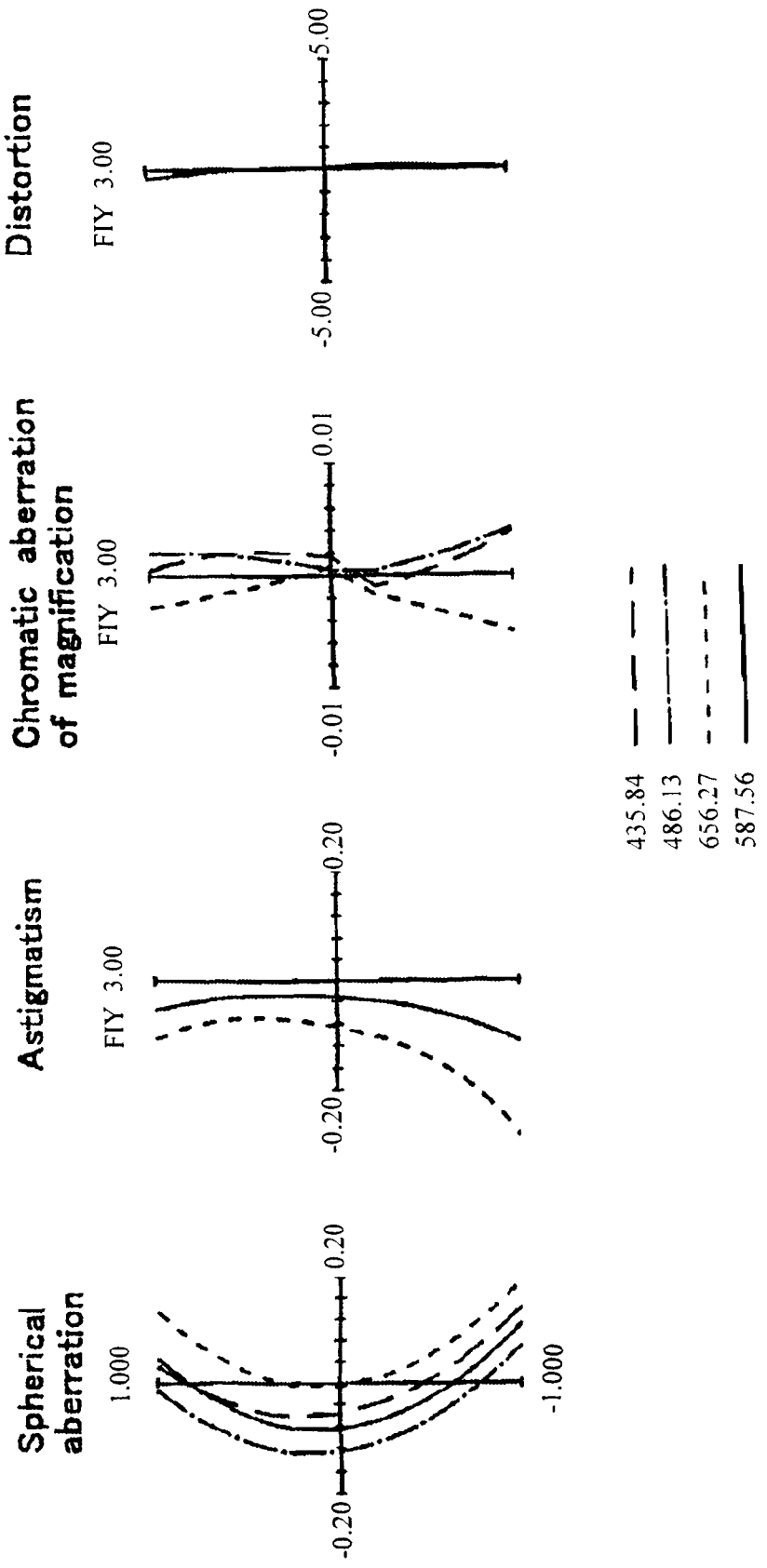

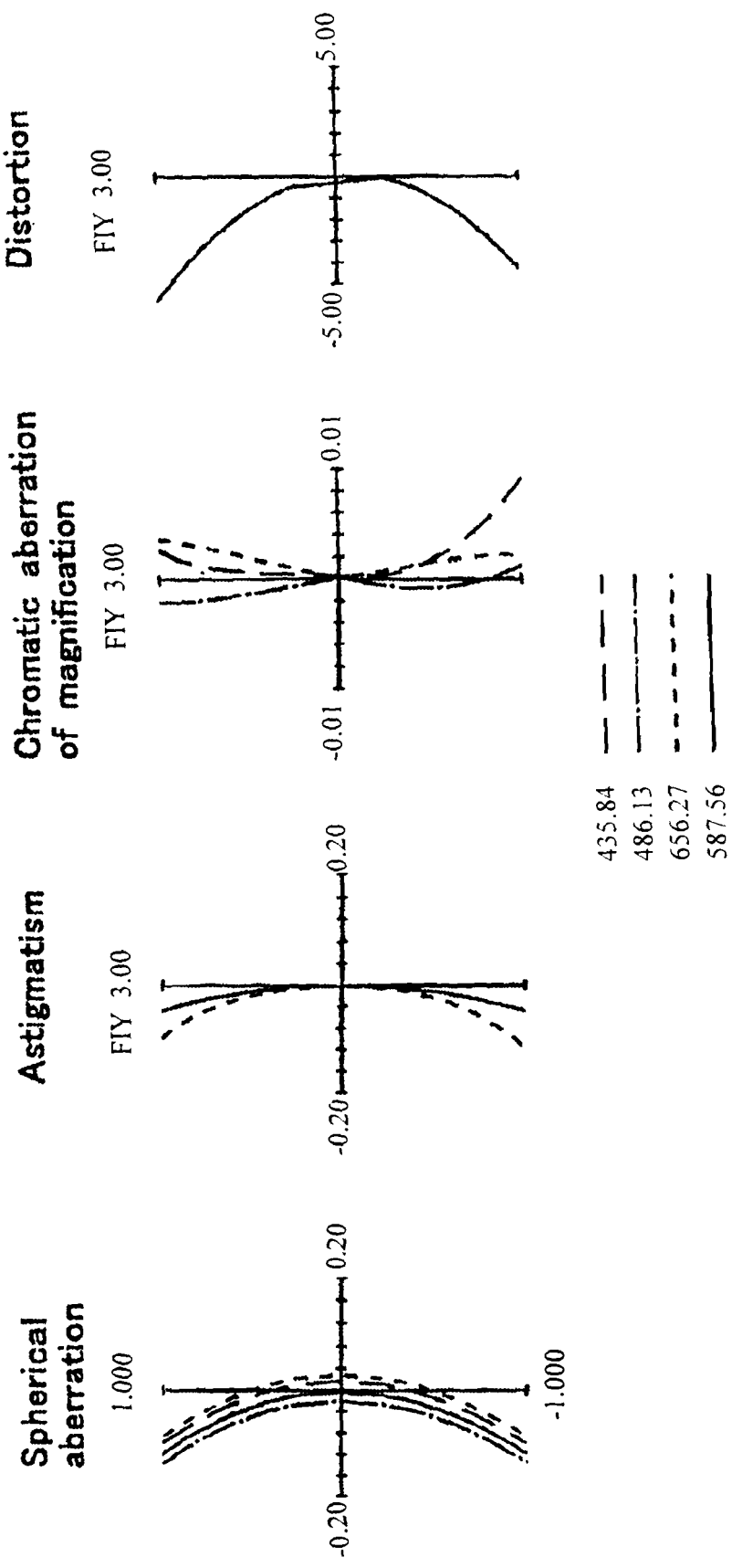

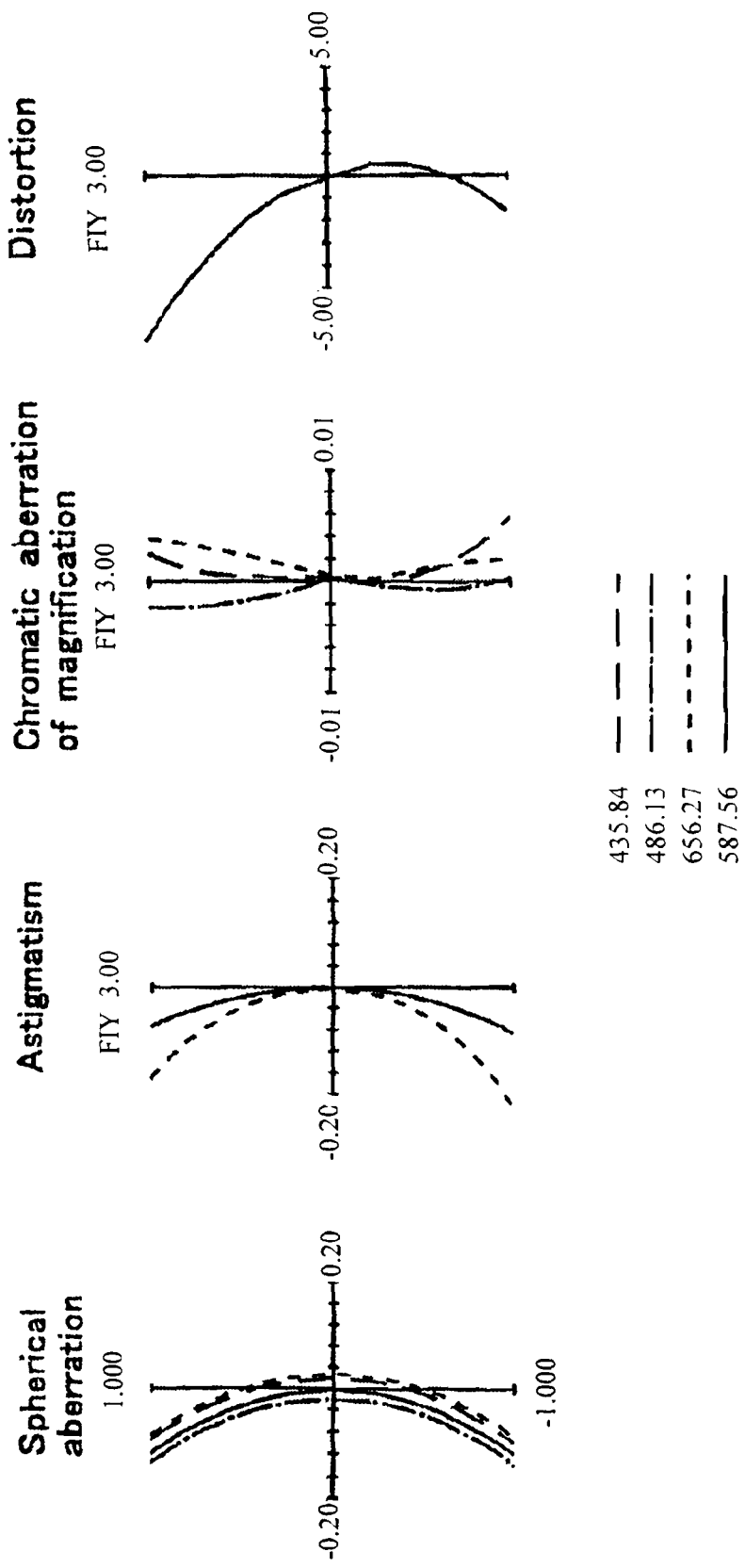

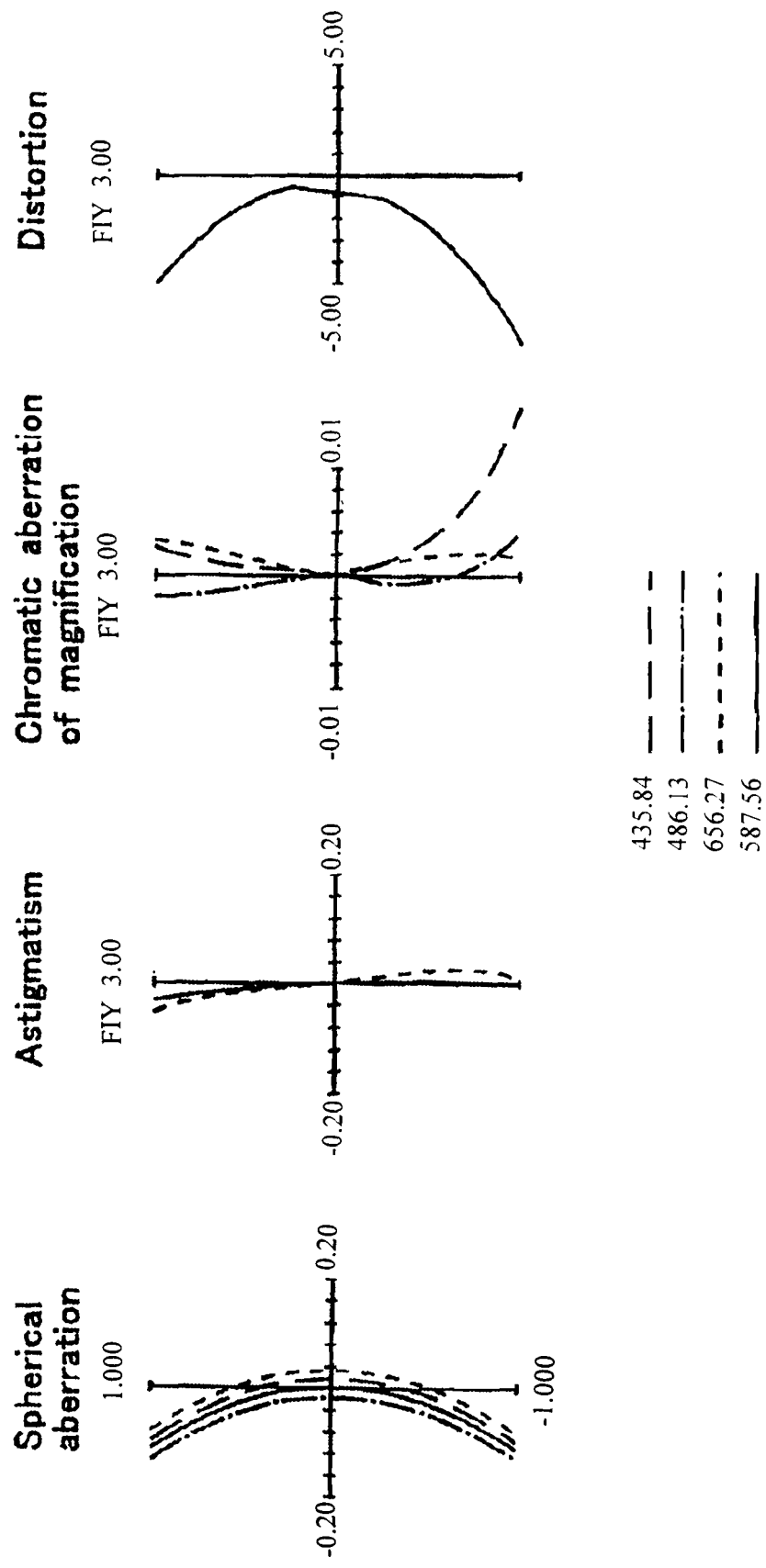

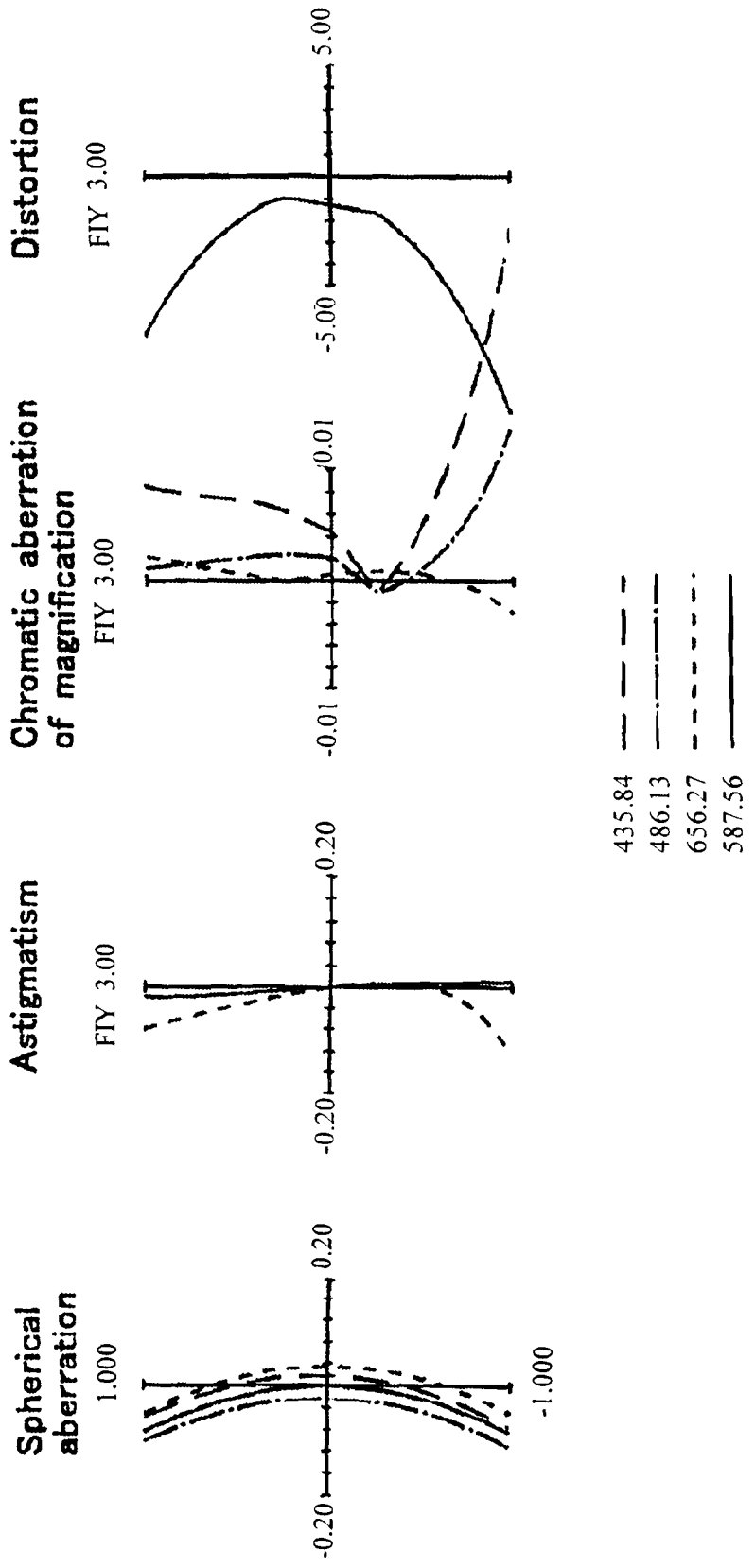
FIG. 11(a) (EXAMPLE 2)

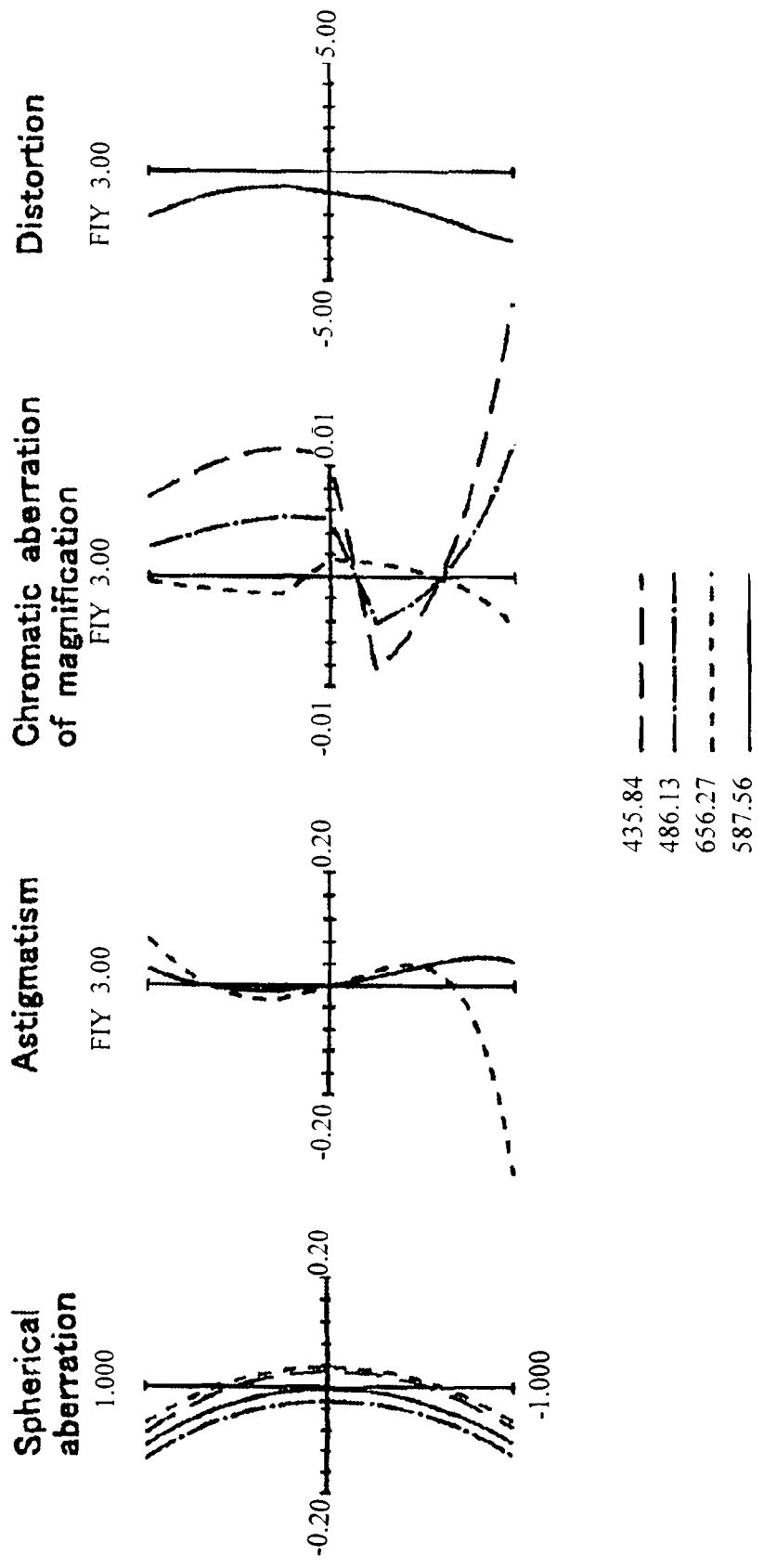
FIG. 11(b) (EXAMPLE 2)

(EXAMPLE 2)

(EXAMPLE 3)

(EXAMPLE 3)

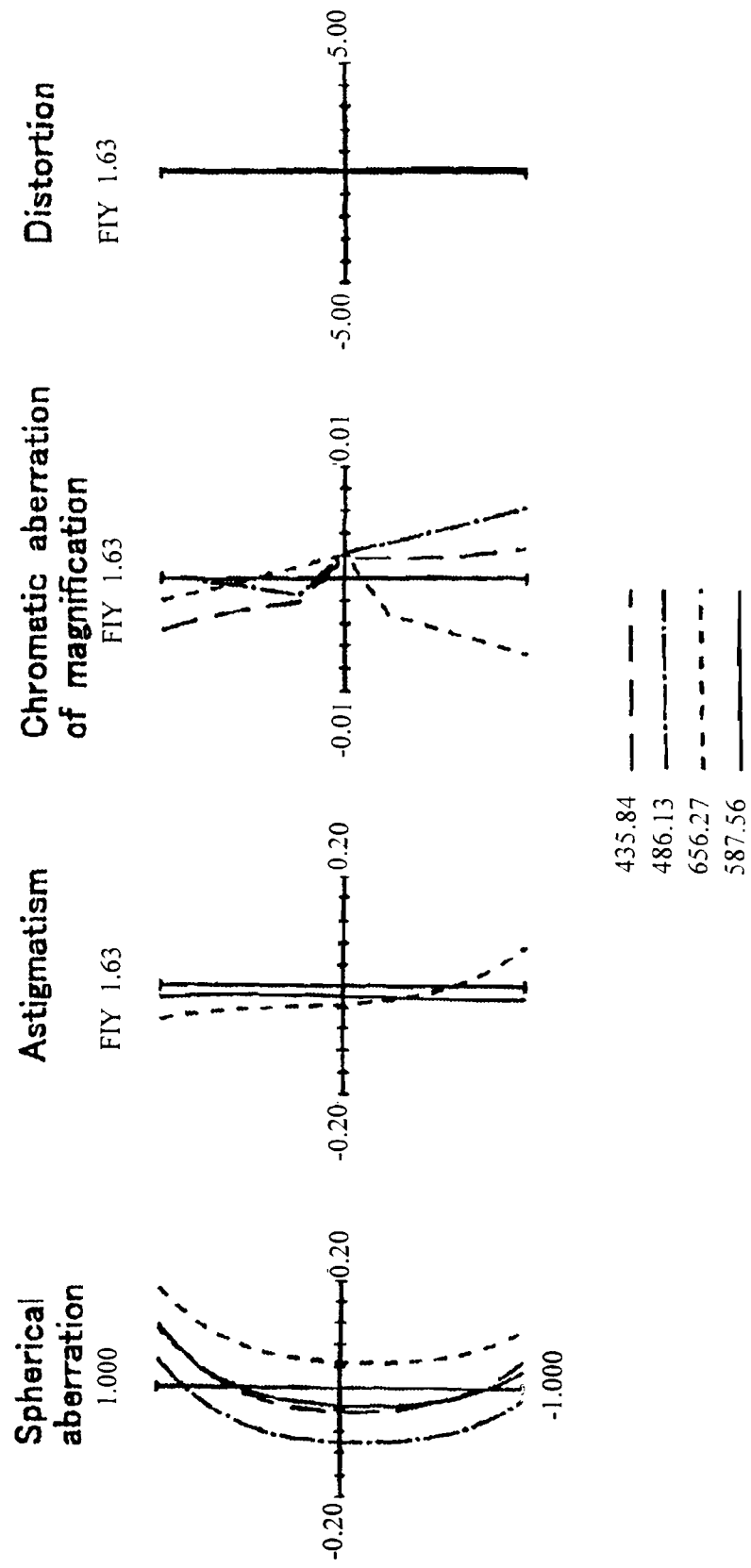
FIG. 12(o) (EXAMPLE 3)

(EXAMPLE 4)

(EXAMPLE 4)

(EXAMPLE 4)

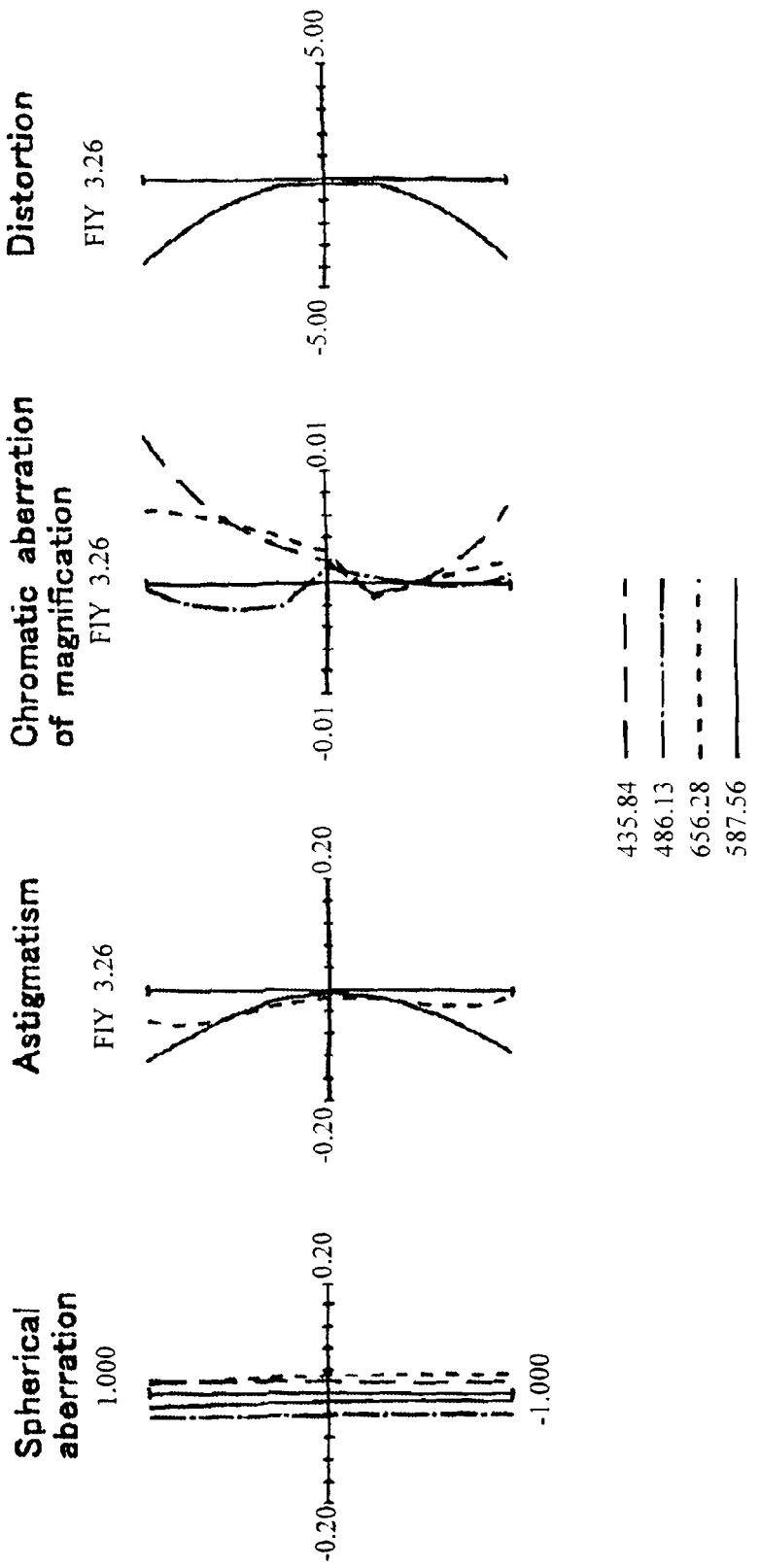
FIG. 14(a) (EXAMPLE 4)

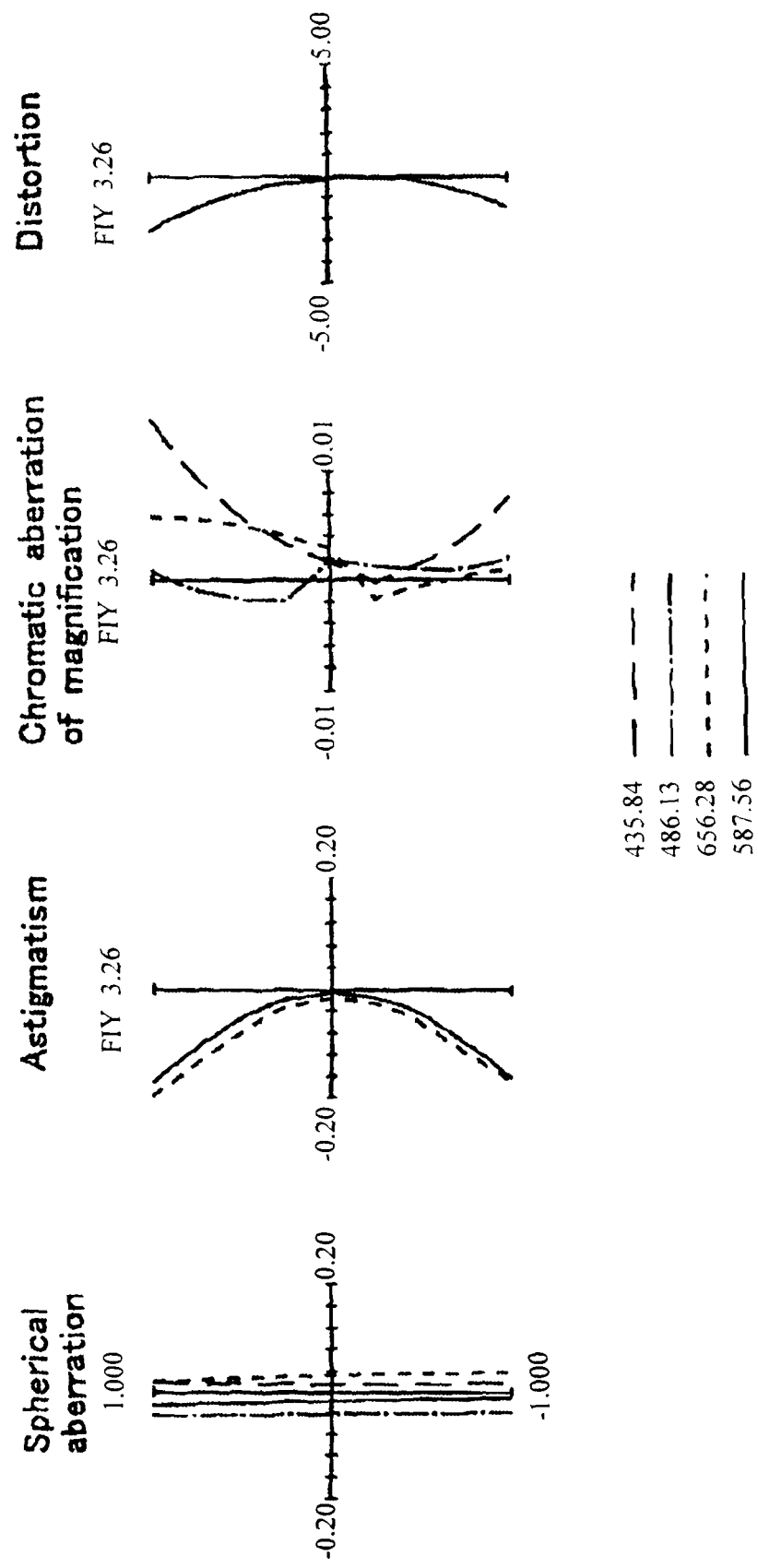

(EXAMPLE 4)

(EXAMPLE 5)

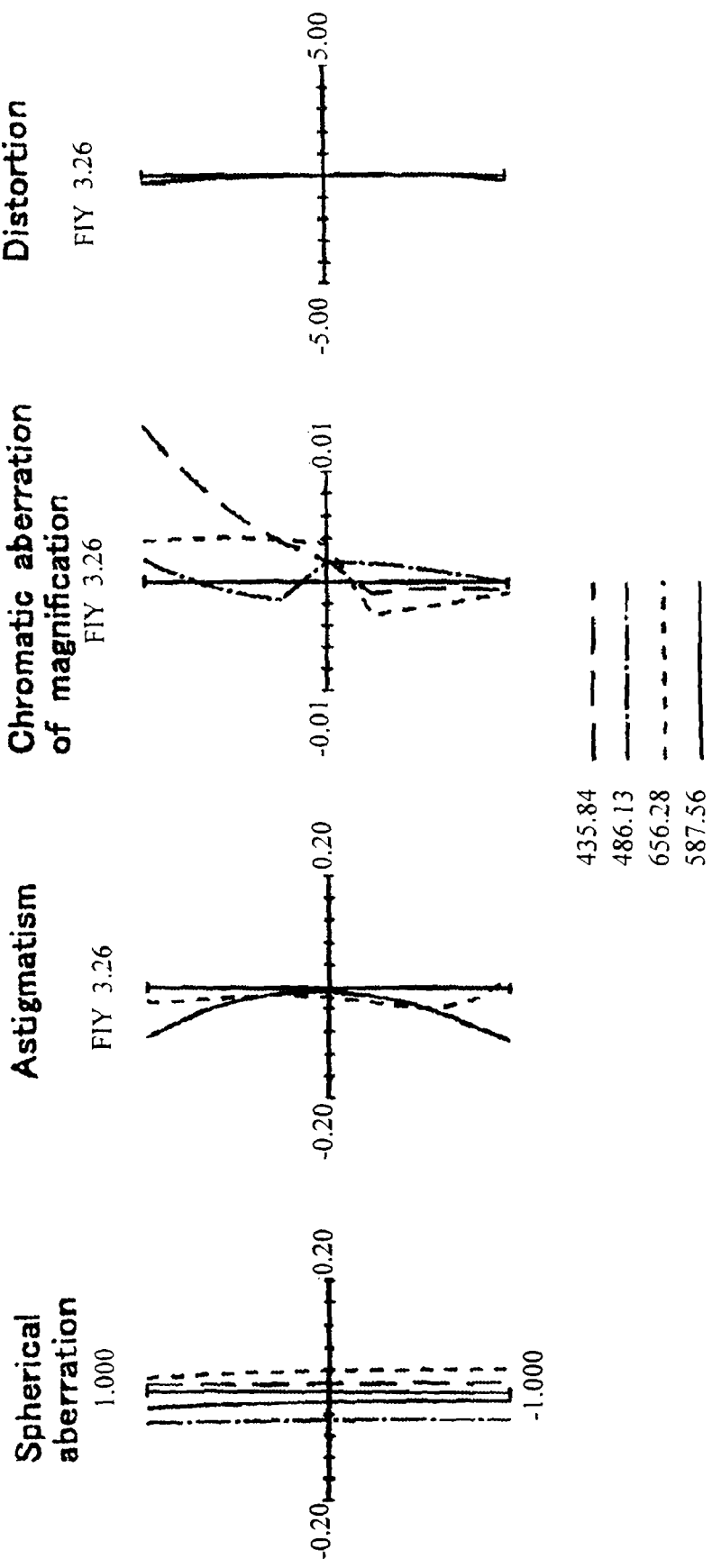

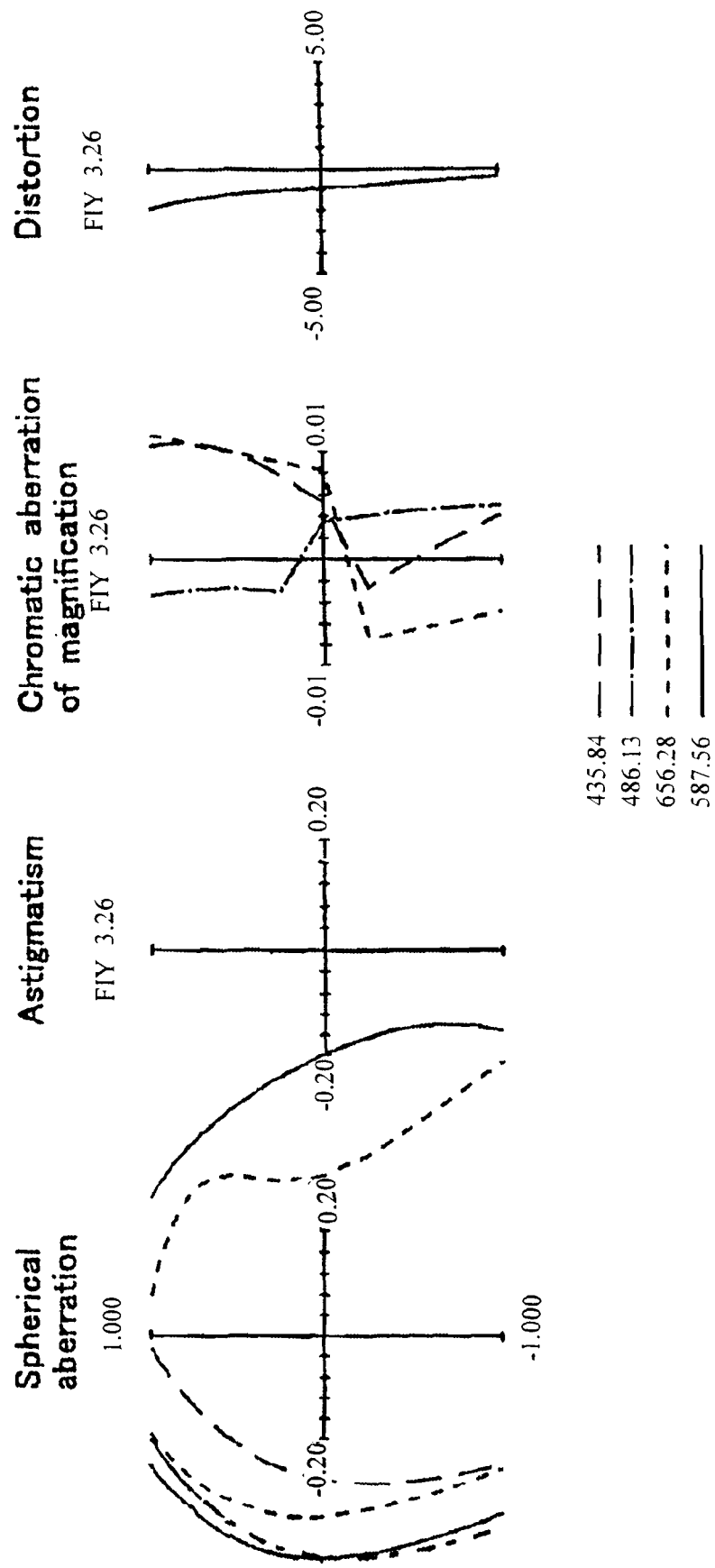
FIG. 15(c) (EXAMPLE 5)

(EXAMPLE 6)

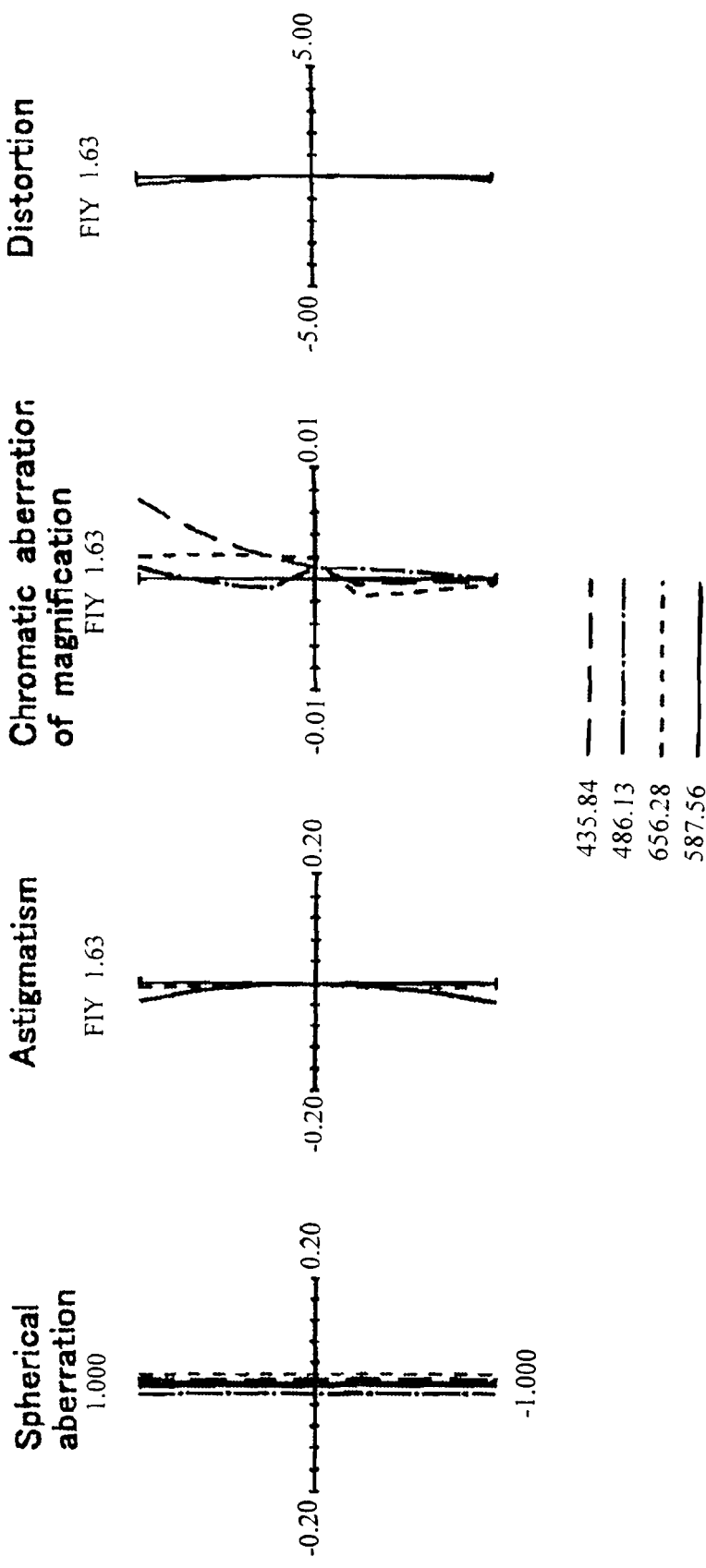

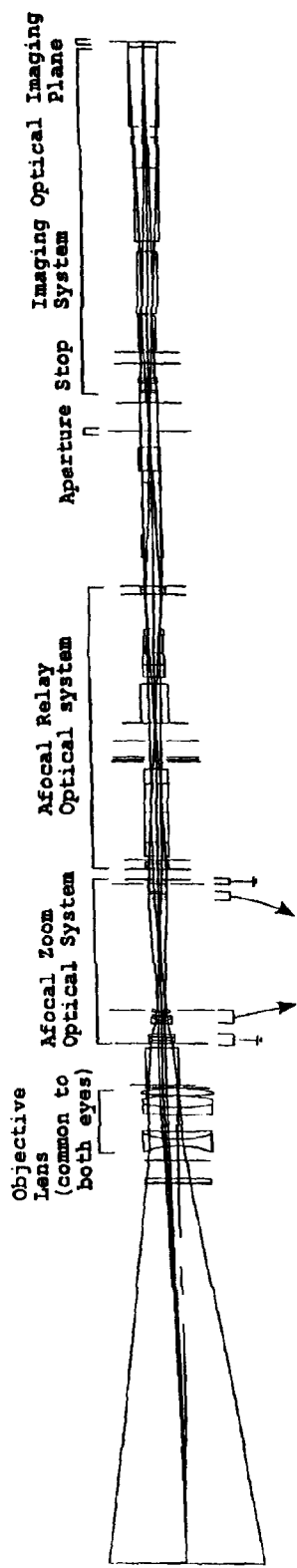
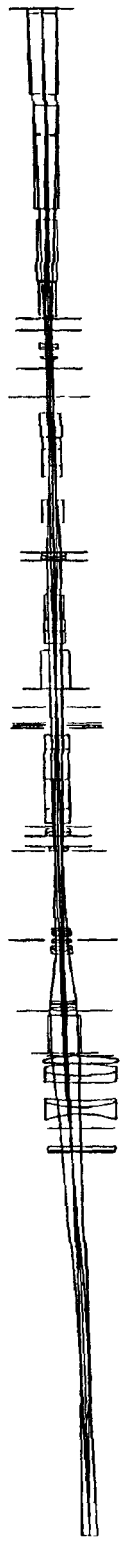
FIG. 17(a) (PRIOR ART)
FIG. 17(b) (PRIOR ART)
FIG. 17(c) (PRIOR ART)

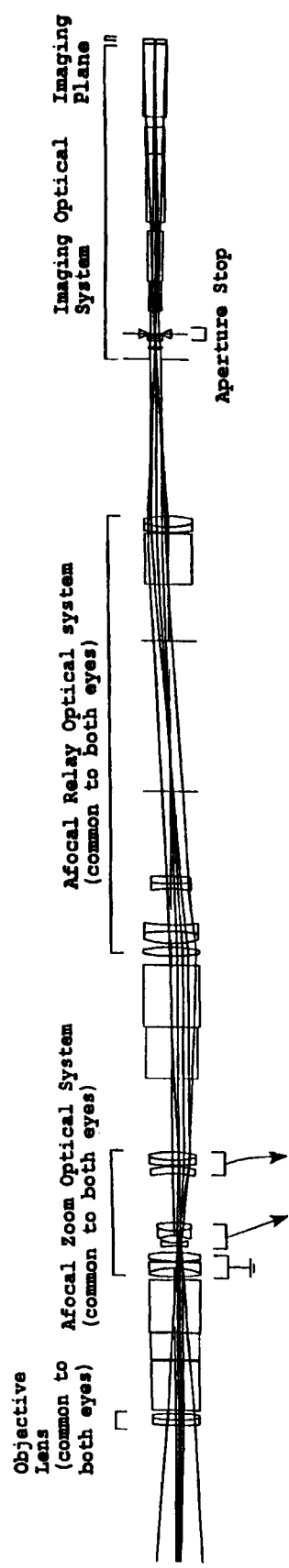
FIG. 18(a) (PRIOR ART)
FIG. 18(b) (PRIOR ART)
FIG. 18(c) (PRIOR ART)

$L_P$: Afocal Relay Length
$L_P \approx 2 \times f_F + 2 \times f_R$

STEREOSCOPIC IMAGING OPTICAL SYSTEM

BACKGROUND OF THE INVENTION

The present invention relates generally to a stereoscopic imaging optical system, and more particularly to an optical system for stereomicroscopes such as operating microscopes.

A stereomicroscope, because of being capable of having a three-dimensional grasp of a minute area, is used in a variety of fields such as studies, inspections, and operations.

A conventional stereomicroscope is of two types: one comprising two independent zoom optical systems for the left eye and the right eye, and another comprising one optical system common to both eyes.

The former is typically set forth in Patent Publication 1, and the latter is typically shown in Patent Publication 2.

There is also a microscope (electron image microscope) wherein an electronic imaging device is located at an imaging position for a viewing optical system, and a stereoscopic image is viewed through a stereoscopic display device instead of an eyepiece lens. An exemplary optical system for the electron image microscope is typically set forth in Patent Publication 3.

A video camera is well known as an electronic imaging apparatus having a zoom optical system. A typical one is shown in Patent Publication 4.

FIG. 17 is illustrative of the first example of the prior art stereomicroscope.

This stereomicroscope comprises a common objective lens for both eyes, a left-and-right pair of afocal zoom lens systems, a left-and-right pair of afocal relay optical systems and a left-and-right pair of imaging optical system.

FIG. 18 is illustrative of the second example of the prior art stereomicroscope.

This stereomicroscope comprises a common objective lens for both eyes, an afocal zoom optical system common to both eyes and coaxial with the objective lens, an afocal relay optical system common to both eyes and coaxial with the objective lens and a left-and-right pair of imaging optical systems.

Such a conventional stereomicroscope as depicted in FIG. 17 has a long total optical length on an image side with respect to the objective lens (a distance from the object-side surface of each afocal zoom optical system to the image plane of each imaging optical system) for the following two main reasons.
1. One reason lies in the optical arrangement per se.
This is chiefly because the following constraint conditions are satisfied.
1-1. Each unit has an independent role.
There are distinctive functions: the afocal zoom optical systems are capable of zooming, and the imaging optical systems are capable of imaging.
1-2 Between the individual units there is an afocal connection.
The afocal connection here means that light rays from an axial object point come substantially parallel out of the zoom optical systems, and enter the imaging optical systems.
This arrangement has one advantage of easy unit replacement.
2. Another reason lies in the optical layout involved (inherent in an optical microscope).
For an optical stereomicroscope it is required to bring a working space (on an operator side) close to a viewing position (an eyepiece lens) thereby allowing the operator to work easily. To this end the arrangement must be laid out such that an optical path from the objective lens to the eyepiece lens is bent. However, allowing for space for locating optical path-bending prisms or the like would render the optical path longer.

Such a conventional stereomicroscope as depicted in FIG. 18, too, has a long total optical length on an image side with respect to the objective lens (a distance from the object side surface of the afocal zoom optical system to the image plane of each imaging optical system) for the following two main reasons.
1. One reason lies in the optical arrangement per se.
The afocal relay optical system projects an image from an aperture stop onto near the object side of the afocal zoom optical system to keep low the height of off-axis rays near the objective lens and the afocal zoom optical system. This works in favor of diameter reductions near the objective lens and the afocal zoom optical system. Especially for the type comprising the common afocal zoom optical system for both eyes, the afocal relay optical system works in favor of diameter reductions.
However, the afocal relay optical system accounts for a large part of the total optical length. In other words, reducing the size of the afocal relay optical system is effective for reductions of the total optical length.
2. Another reason lies in the optical layout involved (inherent in the optical microscope).
Like such a conventional stereomicroscope as depicted in FIG. 17, there is a constraint condition for optical path bending.

In Patent Publication 3, there is an electron image microscope set forth, in which an entrance pupil position is located between an objective optical system and an object (subject) to keep good perspective. There is nothing disclosed about the possibility of size reductions incidental upon electronization.

In Patent Publication 4, there is an optical system for video cameras set forth, which is a 2D optical system for taking one image per one object, not that for stereoscopic imaging. There is nothing stated about a possible application to a stereomicroscope for stereoscopic viewing.

If a stereomicroscope is designed for electronic imaging, there is then none of the constraints of the aforesaid optical layout. The electron image microscope gives relative freedom to the relative position between working space (on the operator side) and the viewing position (stereoscopic display device). The electron image microscope with an electronic imaging device located at an imaging position is designed to convert an optical image into electric signals for displaying it on the stereoscopic display device. Between an imaging system and a display system there is an electric connection that enables the stereoscopic display device to be located at a free position. To have an optical system fit for the electron image microscope, it is important to reconsider the optical arrangement per se while taking the above merits (lifting off the constraint conditions) into account.

Patent Publication 1: JP(A) 2004-109487
Patent Publication 2: JP(A) 10-282428
Patent Publication 3: JP(A) 2006-158452
Patent Publication 4: JP(A) 2000-206407

SUMMARY OF THE INVENTION

Having been made in view of such problems with the prior art, the present invention has for its object to provide a stereoscope imaging optical system that has a total optical length enough short to be fit for an electron image microscope.

According to the invention, the above object is accomplishable by the provision of a stereoscopic imaging optical system comprising, in order from its object side, one objective lens and a plurality of zoom imaging optical systems, characterized in that:

each of said zoom imaging optical systems comprises, in order from its object side, a positive first group, a negative second group, an aperture stop, a positive third group and a positive fourth group, wherein:

said second group moves on an optical axis for zooming, said fourth group moves on the optical axis in association with said second group for correcting an image position fluctuation incidental on zooming, and the following conditions are satisfied:

$$-1 < mg_{rw} < -0.2 \quad (1)$$

$$-0.4 < \Delta_{G4}/\Delta_{G2} < 0.4 \quad (2)$$

where $mg_{rw}$ is the imaging magnification at a low zoom ratio end of the whole of the groups on an image side with respect to the aperture stop, $\Delta_{G4}$ is a difference in an optical axis direction between the position of the fourth group at a low zoom ratio end and the position of the fourth group at a high zoom ratio end provided that + is on the image side, and $\Delta_{G2}$ is a difference in an optical axis direction between the position of the second group at a low zoom ratio end and the position of the second group at a high zoom ratio end provided that + is on the image side.

Referring to how the stereoscopic imaging optical system works, it is most effective for the conventional optical system of the above first type to reduce the size of the zoom optical system. In the above first conventional example, as described above, 1-1. each unit has an independent role, and 1-2. there is an afocal connection between the individual units. For those reasons, the total optical length grows long.

In the invention, the four lens groups have an integrally combined zoom and imaging function, and take on a one unit form as a whole. Referring to the refracting power profile here, the first and second groups on the object side with respect to the aperture stop have generally negative refracting power, and after passing through the third group, light is in a substantially afocal state, and imaged at the fourth group. Main zooming is implemented by moving the second group on the optical axis, and correction of an image position in association with zooming is implemented at the fourth group.

The aperture stop is located between the second and the third group so that the height of off-axis rays passing through the zoom optical system can be lowered. A space on the object side with respect to the aperture stop is mainly used only for the movement of the second group, while spaces before and after the fourth group are used for correction of the image position in association with zooming. This ensures good zooming efficiency, and works in favor of reducing the total length.

In addition, it is preferable for size reductions to satisfy the above conditions (1) and (2).

Condition (1) defines the imaging magnification at low zoom ratio end of the whole of the group located on the image side with respect to the aperture stop.

As the upper limit of −0.2 to Condition (1) is exceeded, it causes zooming efficiency to go worse, working against size reductions. As the lower limit of −1 to Condition (1) is not reached, it may work for zooming but against aberration correction.

Condition (2) defines the amount-of-movement ratio between the second group and the fourth group that move during zooming. As the upper limit of 0.4 to condition (2) is exceeded, it causes the fourth group to be likely to interfere with an optical member near the image plane position at a high zoom ratio end. As the lower limit of −0.4 to Condition (2) is not reached, it causes the fourth group to be likely to interfere with the third group at a high zoom ratio end. As there are deviations from the upper and lower limits of Condition (2), it causes zooming efficiency to go worse, working against size reductions.

The invention has a main advantage of shortening the length of the optical system on the image side with respect to the objective lens.

Besides, the invention has some other advantages.

The invention works for reducing the diameter of the optical system and designing the optical system as a wide-angle arrangement. This is because the aperture stop is located at the center of the zoom imaging optical system as described above, so that the height of off-axis rays passing through the zoom optical system can be lowered.

The invention is suited for an electronic imaging device. On the image side with respect to the aperture stop there are the positive third group and the positive fourth group: there is a substantially telecentric arrangement achieved on the image side. This ensures that the angle of incidence of rays onto the electronic imaging device is much the same at the center and periphery of the associated screen.

The invention works for mechanical arrangements. Moving parts are the second and the fourth group that are separate from each other so that they are less likely to interfere with each other.

In the invention, it is possible to leave out the afocal relay system. In other words, the afocal relay system may be located in conformity to the layout of the microscope body whenever necessary.

In a preferable embodiment of the invention, there is a stereoscopic imaging optical system provided which comprises, in order from its object side, one objective lens and a plurality of zoom imaging optical systems, wherein:

said objective lens comprises a negative front group and a positive rear group;

said zoom imaging optical system comprises, in order from its object side, a positive first group, a negative second group, an aperture stop, a positive third group and a positive fourth group;

any one of the front and the rear group in said objective lens moves on an optical axis to implement focusing for changing a working distance, said second group of said zoom imaging optical system moves on the optical axis for zooming, and said fourth group moves on the optical axis in association with said second group to correct an image position fluctuation in association with zooming; and the following conditions (1) and (2) are satisfied:

$$-1 < mg_{rw} < -0.2 \quad (1)$$

$$-0.4 < \Delta_{G4}/\Delta_{G2} < 0.4 \quad (2)$$

where $mg_{rw}$ is the imaging magnification at a low zoom end of the whole of the groups on an image side with respect to the aperture stop, $\Delta_{G4}$ is a difference in an optical axis direction between the position of the fourth group at a low zoom ration end and the position of the fourth group at a high zoom ratio end provided that + is on the image side, and $\Delta_{G2}$ is a difference in an optical axis direction between the position of the second group at a low zoom ratio end and the position of the second group at a high zoom ratio end provided that + is on the image side.

With the inventive stereoscopic imaging optical system, focusing for changing a working distance (WD) is implemented by the common objective lens for both eyes located nearest to the object side. When an optical system for a sub-viewer is added to that for a main viewer, a total of three or four zoom optical systems must be provided. If focusing is implemented by the common objective lens for both eyes, it is then possible to simplify the mechanical arrangement and control involved.

Because the objective lens is on the object side of the zoom optical system, the amount of movement of the lens is not dependent on a zoom position. Given the WD determined, the amount of movement may be same from the low to the high zoom ratio end. Further, the mechanical arrangement and control involved can be simplified.

According to a more preferable embodiment of the invention, there is a stereoscopic imaging optical system provided which comprises, in order from its object side, one objective lens and a plurality of zoom imaging optical systems, characterized in that:

said objective lens comprises a negative front group and a positive rear group; and each of said zoom imaging optical systems comprises, in order from its object side, a positive first group, a negative second group, an aperture stop, a positive third group and a positive fourth group, wherein:

any one group in said objective lens moves on an optical axis to implement focusing for changing a working distance;

said second group of each zoom imaging optical system moves on the optical axis for zooming;

said fourth group of each zoom imaging optical system moves on the optical axis in association with said second group for correction of an image position fluctuation incidental to zooming; and the following conditions (1') and (2') are satisfied:

$$-0.6 < mg_{rw} < -0.3 \quad (1')$$

$$-0.1 < \Delta_{G4}/\Delta_{G2} < 0.3 \quad (2')$$

where $mg_{rw}$ is the imaging magnification at a low zoom end of the whole of the groups on an image side with respect to the aperture stop, $\Delta_{G4}$ is a difference in an optical axis direction between the position of the fourth group at a low zoom ratio end and the position of the fourth group at a high zoom ratio end provided that + is on the image side, and $\Delta_{G2}$ is a difference in an optical axis direction between the position of the second group at a low zoom ratio end and the position of the second group at a high zoom ratio end provided that + is on the image side.

For the above arrangement, it is more preferable that the lower and upper limits of Condition (1) should be −0.6 and −0.3 (Condition (1')), respectively, and the lower and upper limits of Condition (2) should be 0.1 and 0.3 (Condition (2')), respectively.

In the above embodiments of the invention, the number of the zoom optical systems is not limited to 2: it may be three or more. The reason is that, as described in conjunction with the function of the above objective lens, there is an occasion where an optical system for the sub-viewer is added to that for the main viewer, there is an occasion where an optical path for special light imaging is added to that for visible light imaging, etc.

The present invention also provides a stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following condition (3) is satisfied:

$$0.5 < f_F/L_Z < 0.9 \quad (3)$$

where $f_F$ is the focal length of the front group in the afocal relay optical system, and $L_Z$ is the maximum value of a distance from the surface located nearest to the object side to the surface located nearest to the image side of the afocal zoom optical system.

Reference is now made to how this stereoscopic imaging optical system works. For the above second type of conventional optical system having a common afocal zoom optical system for both eyes, the afocal relay optical system is effective for diameter reductions, and should not be left out. In other words, it is most important for the above second type of conventional optical system to reduce the size of the afocal relay optical system.

With reference to FIG. 19 (that is the same as the prior art example of FIG. 18), consider here what is constructed of the afocal relay optical system. Optical length may be approximated by the following formula:

$$L_P \cong (2 \cdot f_F) + (2 \cdot f_R)$$

where $L_P$ is the optical length of the afocal relay optical system (that is a distance from the aperture stop to an image from the aperture stop), $f_F$ is the focal length of the front group in the afocal relay optical system, and $f_R$ is the focal length of the rear group in the afocal relay system.

To make the optical length $L_P$ of the afocal relay optical system short, it is required to set $f_F$ and $f_R$ at right values.

It is desired that the value of $f_F$ be a bit smaller than the length of the afocal zoom optical system (a factor of 0.5 to 0.9).

As the lower limit of 0.5 to Condition (3) is not reached, there is a shortage of pupil projection distance, which may otherwise result in an increase in the diameter of the zoom optical system and objective lens. As the upper limit of 0.9 to Condition (3) is exceeded, the pupil projection distance is in excess, resulting in an increase in the total optical length.

A chief advantage of the invention is that the length of the optical system can be shortened.

The front group in the afocal relay optical system can have the minimum necessary focal length so that the distance ($2 \cdot f_F$) up to an intermediate imaging plane can be shortened (the right side, first term of $L_P \cong (2 \cdot f_F) + (2 \cdot f_R)$ Further, the present invention provides a stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following condition (4) is satisfied:

$$1.1 < f_F/f_R < 2 \quad (4)$$

where $f_F$ is the focal length of the front group in the afocal relay optical system, and $f_R$ is the focal length of the rear group in the afocal relay optical system.

Referring to the function of this stereoscopic imaging optical system, there is another way of shortening the optical length of the afocal relay optical system. It is then desired that the value of $f_R$ be smaller than that of $f_F$ (by a factor of 1/1.1 to 1/2) thereby shortening the optical length of re-forming an image at the front group in the afocal relay optical system.

As the lower limit of 1.1 to Condition (4) is not reached, there is an increase in the total optical length, and as the upper limit of 2 to Condition (4) is exceeded, it causes the left and right two imaging optical systems to be likely to interfere.

A chief advantage of the invention here is that the afocal relay rear group can have the minimum necessary focal length so that the distance $(2 \cdot f_R)$ from the intermediate imaging plane to the aperture stops can be shortened (the right side, second term of $L_F \cong (2 \cdot f_F) + (2 \cdot f_R)$ Other advantage is that the diameter of the stereoscopic imaging optical system near the imaging optical systems can be made small.

This is because $f_F/f_R$ is greater than 1 so that the diameter of a center beam can be reduced on the image side.

Yet further, the present invention provides a stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following conditions (3) and (4) are satisfied:

$$0.5 < f_F/L_Z < 0.9 \qquad (3)$$

$$1.1 < f_F/f_R < 2 \qquad (4)$$

where $f_F$ is the focal length of the front group in the afocal relay optical system, $f_R$ is the focal length of the rear group in the afocal relay optical system, and $L_Z$ is the maximum value of a distance from the surface nearest to the object side to the surface nearest to the image side of the afocal zoom optical system.

More preferably in the invention, the above conditions (3) and (4) should be satisfied at the same time.

Still further, the present invention provides a stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following conditions (3), (4) and (5) are satisfied:

$$0.5 < f_F/L_Z < 0.9 \qquad (3)$$

$$1.1 < f_F/f_R < 2 \qquad (4)$$

$$5 < fm/IH < 16 \qquad (5)$$

where $f_F$ is the focal length of the front group in the afocal relay optical system, $f_R$ is the focal length of the rear group in the afocal relay optical system, $L_Z$ is the maximum value of a distance from the surface nearest to the object side to the surface nearest to the image side of the afocal zoom optical system, fm is the focal length of each imaging optical system, and IH is the maximum image height on an imaging device located at an image position of the imaging optical system.

The stereoscopic imaging optical system here should better satisfy Condition (5) that is concerned with size reductions of the imaging optical systems, and defines the focal length of the imaging optical systems and the size of the imaging device (the maximum image height).

As the upper limit of 16 to Condition (5) is exceeded, the optical length of the imaging optical systems grows long, and as the lower limit of 5 to Condition (5) is not reached, it works against correction of aberrations of the imaging optical systems.

Still further, the present invention provides a stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following conditions (3'), (4') and (5') are satisfied:

$$0.6 < f_F/L_Z < 0.9 \qquad (3')$$

$$1.1 < f_F/f_R < 1.8 \qquad (4')$$

$$7 < fm/IH < 15 \qquad (5')$$

where $f_F$ is the focal length of the front group in the afocal relay optical system, $f_R$ is the focal length of the rear group in the afocal relay optical system, $L_Z$ is the maximum value of a distance from the surface nearest to the object side to the surface nearest to the image side of the afocal zoom optical system, fm is the focal length of each imaging optical system, and IH is the maximum image height on an imaging device located at an image position of the imaging optical system.

More preferably in the invention, the lower and upper limits of Condition (3) should be 0.6 and 0.9 (Condition (3')), respectively; the lower and upper limits of Condition (4) should be 1.1 and 1.8 (Condition (4')), respectively; and the lower and upper limits of Condition (5) should be 7 and 15 (Condition (5')), respectively.

In the above embodiments of the invention, the number of the zoom optical systems is not limited to 2, and may be three or more. The reason is that, as described in conjunction with the function of the above objective lens, there is an occasion where an optical system for the sub-viewer is added to that for the main viewer, there is an occasion where an optical path for special light imaging is added to that for visible light imaging, etc.

It is noted that the invention also includes an operating microscope having any one of the above stereoscopic imaging optical systems.

According to the invention, it is thus possible to provide a stereoscopic imaging optical system that has a total optical length enough short to be well fit for an electron image microscope.

Still other objects and advantages of the invention will in part be obvious and will in part be apparent from the specification.

The invention accordingly comprises the features of construction, combinations of elements, and arrangement of parts which will be exemplified in the constitution hereinafter set forth, and the scope of the invention will be indicated in the claims.

BRIEF DESCRIPTION OF THE DRAWINGS

FIG. 1 is illustrative in lens arrangement section of the stereoscopic imaging optical system of Example 1 upon zooming at (a) a low zoom ratio, (b) an intermediate zoom ratio and (c) a high zoom ratio while at a working distance (WD) of 200 mm.

FIG. 2 is illustrative in lens arrangement section of the stereoscopic imaging optical system of Example 1 upon zooming at a low zoom ratio while at (a) WD=200 mm, (b) WD=100 mm and (c) WD=400 mm.

FIG. 6 is illustrative in lens arrangement section of the stereoscopic imaging optical system of Example 4 upon zooming at a low zoom ration while at (a) WD=200 mm, (b) WD=100 mm and (c) WD=400 mm.

FIG. 7 is illustrative in lens arrangement section of the stereoscopic imaging optical system of Example 5 upon zooming at (a) a low zoom ratio, (b) an intermediate zoom ratio and (c) a high zoom ratio while at a working distance (WD) of 200 mm.

FIG. 10 is indicative of spherical aberrations, astigmatism, chromatic aberration of magnification, and distortion of Example 1 in the states of FIGS. 2(a), 2(b) and 2(c).

FIG. 17 is illustrative in lens arrangement section of the first example of the optical system for a conventional stereomicroscope.

FIG. 18 is illustrative in lens arrangement section of the second example of the optical system for a conventional stereomicroscope.

DESCRIPTION OF THE PREFERRED EMBODIMENTS

Figure 3A:
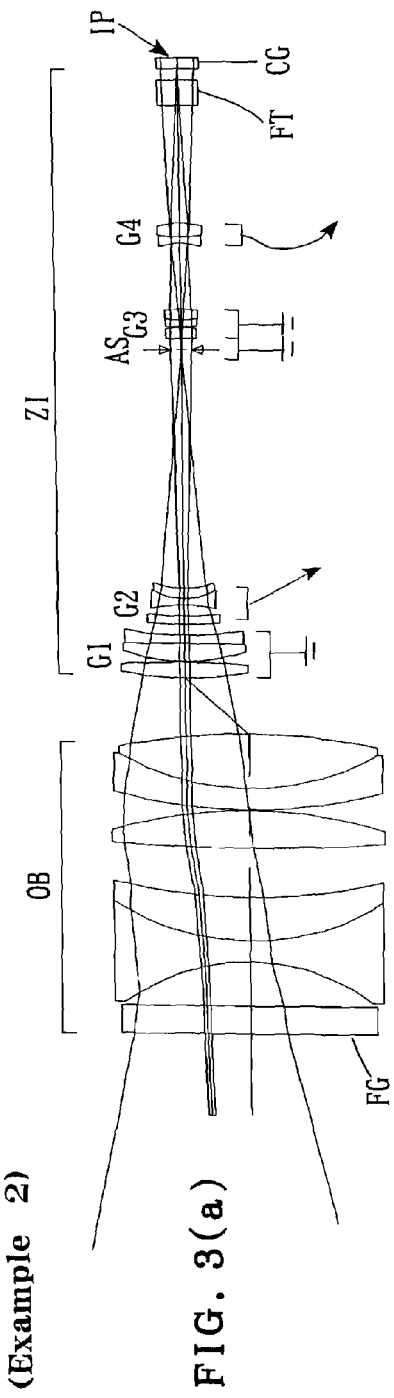
FIG. 3 is illustrative in lens arrangement section of the stereoscopic imaging optical system of Example 2 upon zooming at (a) a low zoom ratio, (b) an intermediate zoom ration and (b) a high zoom ratio (c) while at a working distance (WD) of 200 mm.

The inventive stereoscopic imaging optical system is now explained with reference to Examples 1 to 6.

In the lens arrangement sections of the stereoscopic imaging optical systems of Examples 1-6, the objective lens system is indicated by OB, the zoom imaging optical system by ZI, the afocal zoom optical system by AZ, the afocal relay optical system by AL, the front and rear groups in the afocal relay optical system by GF and GR, respectively, the imaging optical system by IL, the intermediate image by IM, the end cover glass by FG, optical members (plane-parallel plates), for which infrared cut filters, optical low-pass filters, dichroic mirrors or the like are presumed, by FT, the CCD chip sealing glass by CG, the aperture stop by AS, the flare stop by FS, and the imaging plane (image plane) by IP.Out of these lens arrangement sections, surface numbers of optical surfaces and surface-to-surface spaces are omitted for the purpose of simplifying illustrations.

In Examples 1-6, sapphire is used as the material of the end cover glass FG but, of course, other materials resistant to sterilization may be used. Alternatively, general optical glasses may be used as well.

Numerical data about Examples 1-6 will be given later. It is here noted that the optical surface numbers are given by Nos. as counted from the front surface of the end cover glass FG, and that the radius of curvature, the surface-to-surface spaces or air spaces, the d-line refractive index, and the Abbe constants are indicated by "r", "d", "nd", and "vd", respectively. The radius of curvature, and the surface-to-surface space is given in mm.

FIG. 1 is illustrative in lens arrangement section of the stereoscopic imaging optical system of Example 1 upon zooming at (a) a low zoom ratio, (b) an intermediate zoom ratio and (c) a high zoom ratio while at a working distance (WD) of 200 mm, and FIG. 2 is illustrative in lens arrangement section of the stereoscopic imaging optical system of Example 1 upon zooming at a low zoom ratio while at (a) WD=200 mm, (b) WD=100 mm and (c) WD=400 mm. Throughout the drawings, for the left-and-right pair components, only one is shown, and a center beam at the center of the screen and a chief ray at the periphery of the screen are only shown.

Example 1 is made up of the objective lens optical system OB common to both eyes, and a left-and-right pair of zoom imaging optical systems ZI subsequent to it. Each zoom imaging optical system ZI is made up of a positive first group G1, a negative second group G2, the aperture stop AS, a positive third group G3, and a positive fourth group G4. Upon zooming from a low to a high zoom ratio, the first group G1, the aperture stop AS and the third group G3 remain fixed, while the second group G2 moves monotonously toward the image plane side, and the fourth group G4 first moves toward the object side and then goes back to the image plane side. At the high zoom ration, the fourth group is positioned more on the image plane side than at the low zoom ratio. See FIG. 1.

The objective lens optical system OB is made up of a front group consisting of a cemented lens of a double-concave negative lens and a positive meniscus lens convex on its object side, and a rear group consisting of a cemented lens of a negative meniscus lens convex on its object side and a double-convex positive lens, and a double-convex positive lens. By letting out that rear group toward the object side, the WD is kept long. See FIG. 2.

Referring here to the numerical data given later, Surface Nos. 1 and 2 are the end cover glass FG, Surface Nos. 3-5 are the cemented lens in the front group in the objective lens optical system OB, Surface Nos. 6-8 are the cemented lens in the rear group in the objective lens optical system OB, Surface Nos. 9-10 are the double-convex positive lens in the rear group in the objective lens optical system OB, and Surface Nos. 11 through 31 are the zoom imaging optical system ZI. The first group G1 in the zoom imaging optical system ZI is made up of a double-convex positive lens indicated by Surface Nos. 11 and 12, and a cemented lens of a double-convex positive lens and a double-concave negative lens indicated by Surface Nos. 13, 14 and 15, and the second group G2 is made up of a negative meniscus lens convex on its image plane side, indicated by Surface Nos. 16 and 17 and a cemented lens of a double-concave negative lens and a positive meniscus lens convex on its object side, indicated by Surface Nos. 18, 19 and 20. The aperture stop AS of Surface No. 21 is followed by the third group G3 that is made up of a double-convex positive lens indicated by Surface Nos. 22 and 23 and a cemented lens of a negative meniscus lens convex on its object side and a double-convex positive lens indicated by Surface Nos. 24, 25 and 26, and the fourth group G4 is made up of a cemented lens of a double-concave negative lens and a double-convex positive lens indicated by Surface Nos. 27, 28 and 29. Following this, the optical member (plane-parallel plate) FT indicated by Surface Nos. 30 and 31 is positioned, after which there is the imaging plane (image plane) IP of Surface No. 34 positioned that has the CCD chip sealing glass CG indicated by Surface Nos. 32 and 33.

It should here be noted that a portion from the zoom imaging optical system ZI to the imaging plane IP is decentered 10.5000 mm in the vertical direction to the optical axis of the objective lens optical system OB.

Figure 9A:
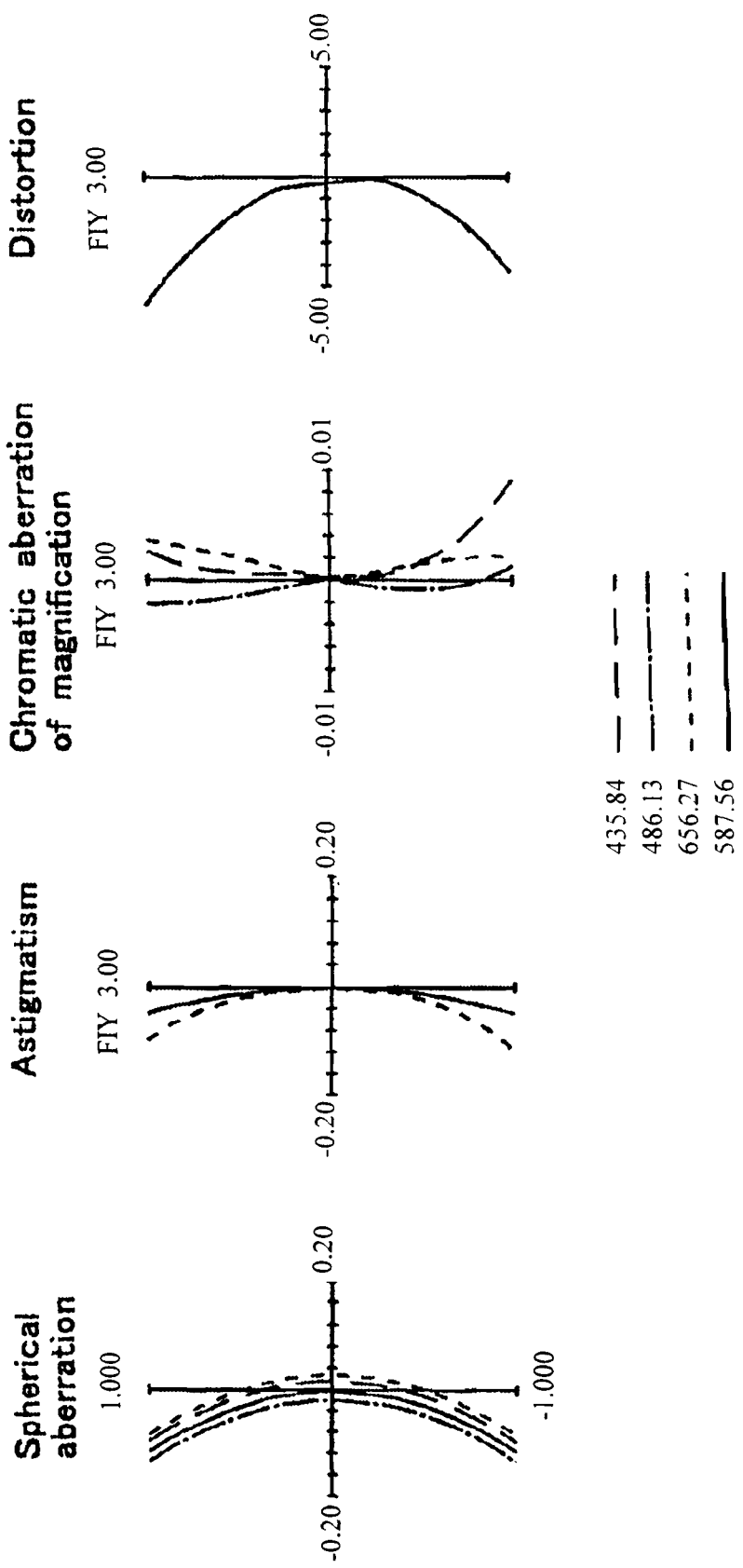
FIG. 9 is indicative of spherical aberrations, astigmatism, chromatic aberration of magnification, and distortion of Example 1 in the states of FIGS. 1(a), 1(b) and 1(c).

The aberration diagrams of this example are presented in FIGS. 9 and 10. FIGS. 9(a), 9(b) and 9(c), and FIGS. 10(a), 10(b) and 10(c) are indicative of spherical aberrations, astigmatisms, chromatic aberrations of magnification and distortions in the states of FIGS. 1(a), 1(b) and 1(c), and FIGS. 2(a), 2(b) and 2(c), respectively. Throughout the drawings, the scale is given by length in mm, the proportion (distortion) is given in %, the wavelength is given in nm, the solid line and broken line for astigmatisms are ΔS and ΔM, respectively, and the image height is indicated by FIY.

FIG. 3 is illustrative in lens arrangement section of the stereoscopic imaging optical system of Example 2 upon zooming at (a) a low zoom ratio, (b) an intermediate zoom ratio and (c) a high zoom ratio while at a working distance (WD) of 200 mm.

Example 2 is made up of the objective lens optical system OB common to both eyes, and a left-and-right pair of zoom imaging optical systems ZI subsequent to it. Each zoom imaging optical system ZI is made up of a positive first group G1, a negative second group G2, the aperture stop AS, a positive third group G3, and a positive fourth group G4. Upon zooming from a low to a high zoom ratio, the first group G1, the aperture stop AS and the third group G3 remain fixed, while the second group G2 moves monotonously toward the image plane side, and the fourth group G4 first moves toward the object side and then goes back to the image plane side. At the high zoom ratio, the fourth group is positioned more on the image plane side than at the low zoom ratio.

The objective lens optical system OB is made up of a front group consisting of a cemented lens of a double-concave negative lens and a positive meniscus lens convex on its object side, and a rear group consisting of a double-convex positive lens and a cemented lens of a negative meniscus lens convex on its object side and a double-convex positive lens. By letting out that rear group toward the object side, the WD is kept long.

Referring here to the numerical data given later, Surface Nos. 1 and 2 are the end cover glass FG, Surface Nos. 3, 4 and 5 are the cemented lens in the front group in the objective lens optical system OB, Surface Nos. 6 and 7 are the double-convex positive lens in the rear group in the objective lens optical system OB, Surface Nos. 8, 9 and 10 are the cemented lens in the rear group in the objective lens optical system OB, and Surface Nos. 11 through 31 are the zoom imaging optical system ZI. The first group G1 in the zoom imaging optical system ZI is made up of a double-convex positive lens indicated by Surface Nos. 11 and 12, and a cemented lens of a double-convex positive lens and a double-concave negative lens indicated by Surface Nos. 13, 14 and 15, and the second group G2 is made up of a negative meniscus lens convex on its object side, indicated by Surface Nos. 16 and 17 and a cemented lens of a double-concave negative lens and a positive meniscus lens convex on its object side, indicated by Surface Nos. 18, 19 and 20. The aperture stop AS of Surface No. 21 followed by the third group G3 that is made up of a double-convex positive lens of Surface Nos. 22-23 and a cemented lens of a negative meniscus lens convex on its object side and a double-convex positive lens indicated by Surface Nos. 24, 25 and 26, and the fourth group G4 is made up of a cemented lens of a double-concave negative lens and a double-convex positive lens indicated by Surface Nos. 27, 28 and 20. Following this, the optical member (plane-parallel plate) FT of Surface Nos. 30 and 31 is positioned, after which there is the imaging plane (image plane) IP of Surface No. 34 positioned that has the CCD chip sealing glass CG indicated by Surface Nos. 32 and 33.

It should here be noted that a portion from the zoom imaging optical system ZI to the imaging plane IP is decentered 10.5000 mm in the vertical direction to the optical axis of the objective lens optical system OB.

Figure 3B:
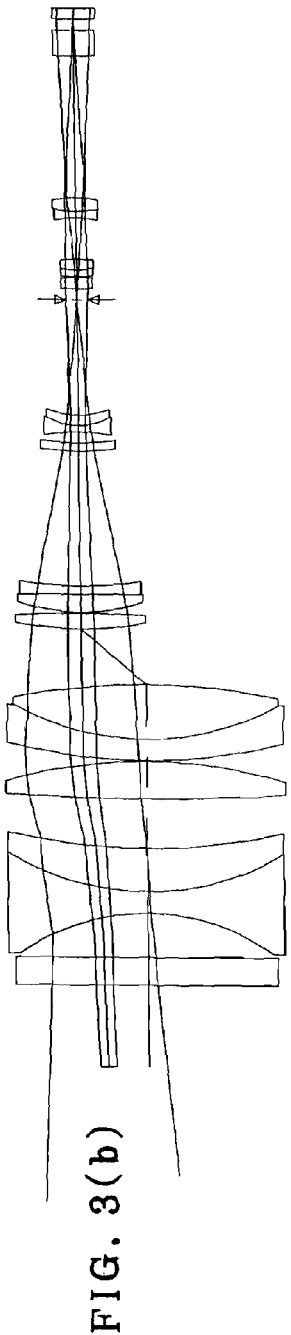
Figure 3C:
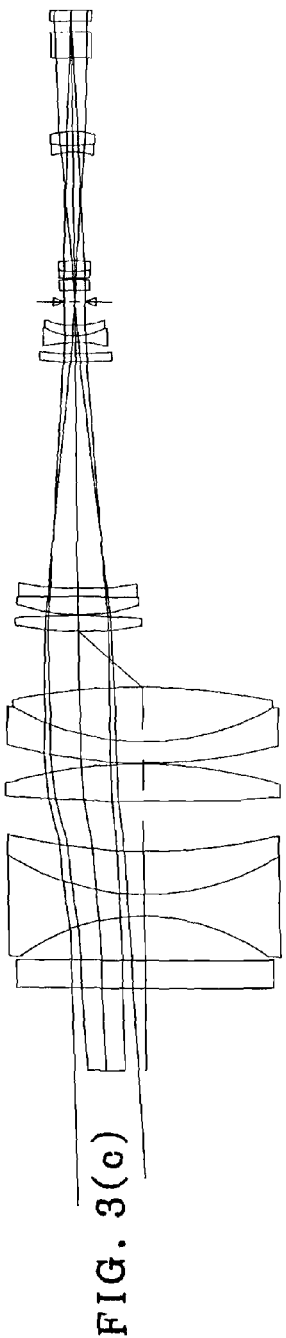
Figure 11C:
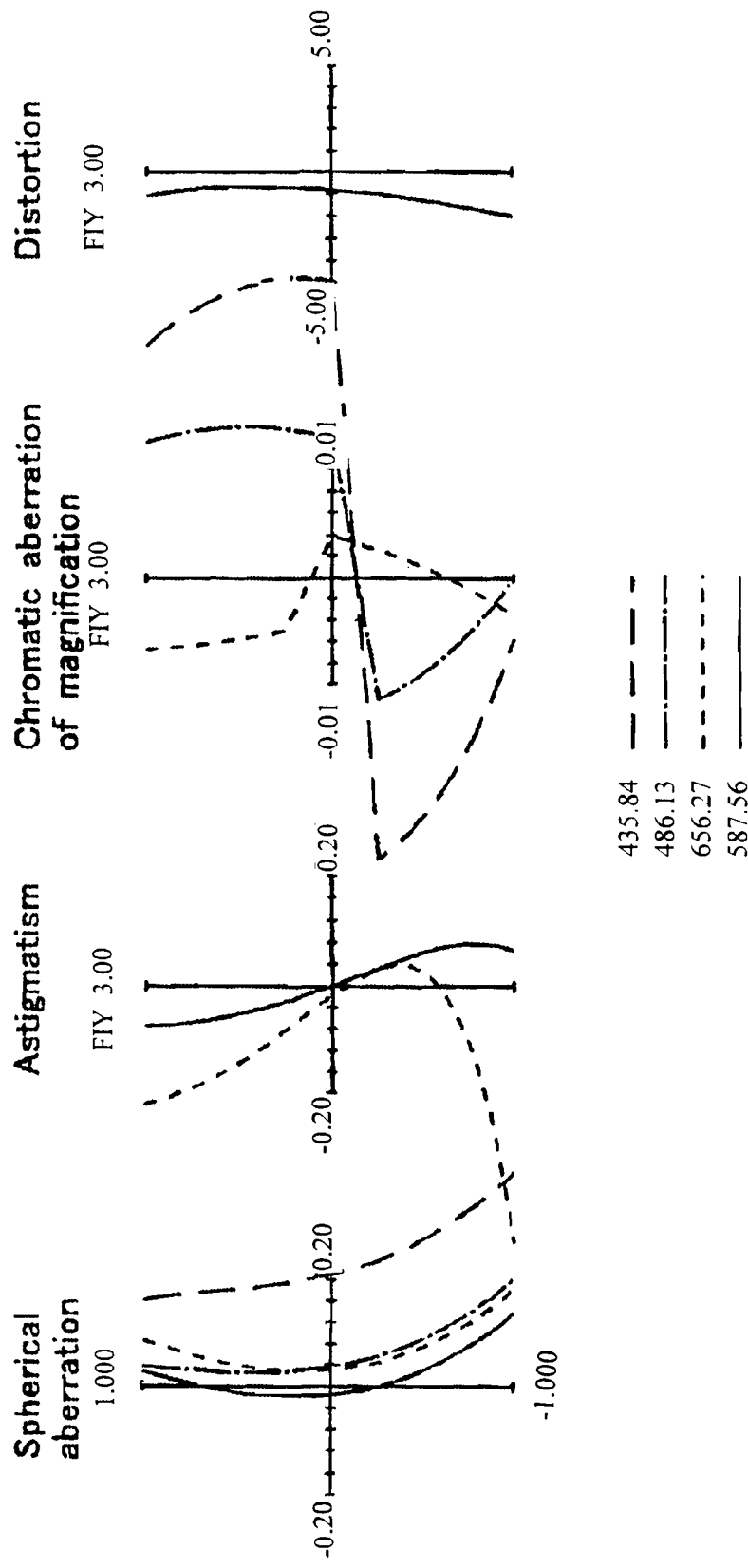
FIG. 11 is indicative of aberrations of Example 2, as in FIGS. 9(a), 9(b) and 9(c) corresponding to FIGS. 3(a), 3(b) and 3(c).

Aberration diagrams of this example similar to FIGS. 9(a), 9(b) and 9(c) corresponding to FIGS. 3(a), 3(b) and 3(c) are presented in FIGS. 11(a), 11(b) and 11(c).

FIG. 4 is illustrative in lens arrangement section of the stereoscopic imaging optical system of Example 3 at (a) a low zoom ratio, (b) an intermediate zoom ratio and (c) a high zoom ratio while at a working distance (WD) of 200 mm.

Example 3 is made up of the objective lens optical system OB common to both eyes, and a left-and-right pair of zoom imaging optical systems ZI subsequent to it. Each zoom imaging optical system ZI is made up of a positive first group G1, a negative second group G2, the aperture stop AS, a positive third group G3, and a positive fourth group G4. Upon zooming from a low to a high zoom ratio, the first group G1, the aperture stop AS and the third group G3 remain fixed, while the second group G2 moves monotonously toward the image plane side, and the fourth group G4 first moves toward the object side and then goes back to the image plane side. At the high zoom ratio, the fourth group is positioned more on the image plane side than at the low zoom ratio.

The objective lens optical system OB is made up of a front group consisting of a cemented lens of a double-concave negative lens and a positive meniscus lens convex on its object side, and a rear group consisting of a cemented lens of a negative meniscus lens convex on its object side and a double-convex positive lens, and a double-convex positive lens. By letting out that rear group toward the object side, the WD is kept long.

Referring here to the numerical data given later, Surface Nos. 1 and 2 are the end cover glass FG, Surface Nos. 3, 4 and 5 are the cemented lens in the front group in the objective lens optical system OB, Surface Nos. 6, 7 and 8 are the cemented lens in the rear group in the objective lens optical system OB, Surface Nos. 9 and 10 are the double-convex positive lens in the rear group in the objective lens optical system OB, and Surface Nos. 11 through 31 are the zoom imaging optical system ZI. The first group G1 in the zoom imaging optical system ZI is made up of a double-convex positive lens indicated by Surface Nos. 11 and 12, and a cemented lens of a positive meniscus lens convex on its object side and a negative meniscus lens convex on its object side, indicated by Surface Nos. 13, 14 and 15, and the second group G2 is made up of a negative meniscus lens convex on its object side, indicated by Surface Nos. 16 and 17 and a cemented lens of a double-concave negative lens and a positive meniscus lens convex on its object side, indicated by Surface Nos. 18, 19 and 20. The aperture stop AS of Surface No. 21 followed by the third group G3 that is made up of a meniscus lens convex on its image plane side, indicated by Surface Nos. 22 and 23, and a cemented lens of a double-convex positive lens and a negative meniscus lens convex on its image plane side, indicated by Surface Nos. 24, 25 and 26, and the fourth group G4 is made up of a cemented lens of a double-concave negative lens and a double-convex positive lens indicated by Surface Nos. 27, 28 and 29. Following this, the optical member (plane-parallel plate) FT indicated by Surface Nos. 30 and 31 is positioned, after which there is the imaging plane (image plane) IP of Surface No. 34 positioned that has the CCD chip sealing glass CG indicated by Surface Nos. 32 and 33.

It should here be noted that a portion from the zoom imaging optical system ZI to the imaging plane IP is decentered 7.5000 mm in the vertical direction to the optical axis of the objective lens optical system OB.

Figure 4A:
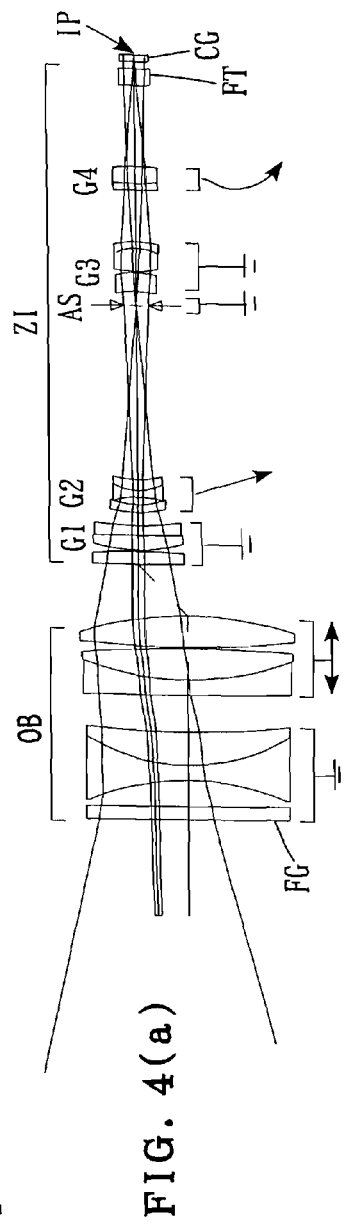
FIG. 4 is illustrative in lens arrangement section of the stereoscopic imaging optical system of Example 3 upon zooming at (a) a low zoom ratio, (b) an intermediate zoom ratio and (c) a high zoom ratio while at a working distance (WD) of 200 mm.
Figure 4B:
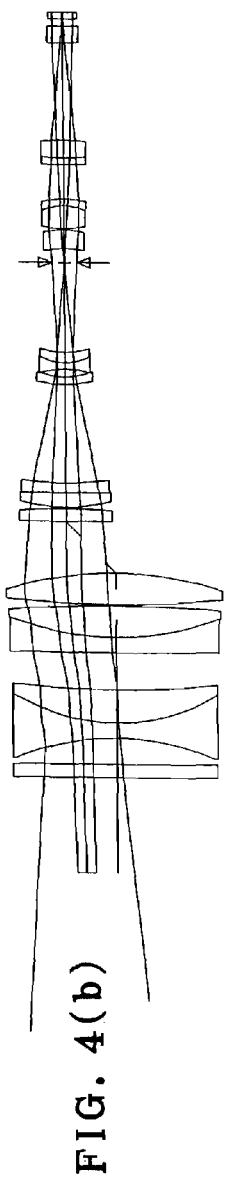
Figure 4C:
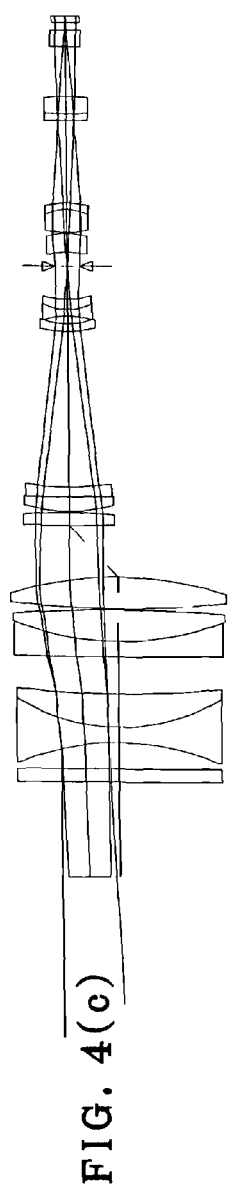
Figure 12A:
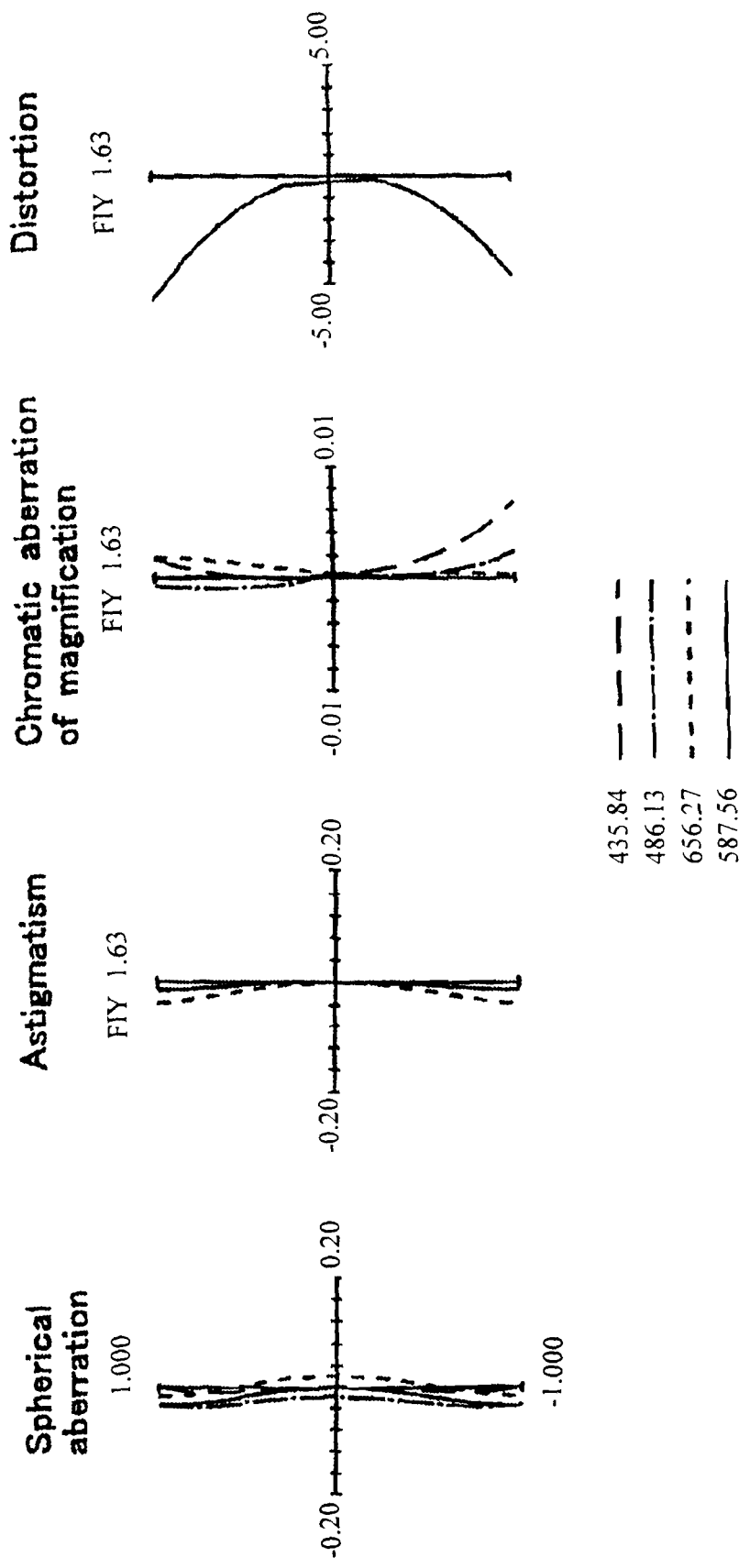
FIG. 12 is indicative of aberrations of Example 3, as in FIGS. 9(a), 9(b) and 9(c) corresponding to FIGS. 4(a), 4(b) and 4(c).
Figure 12B:
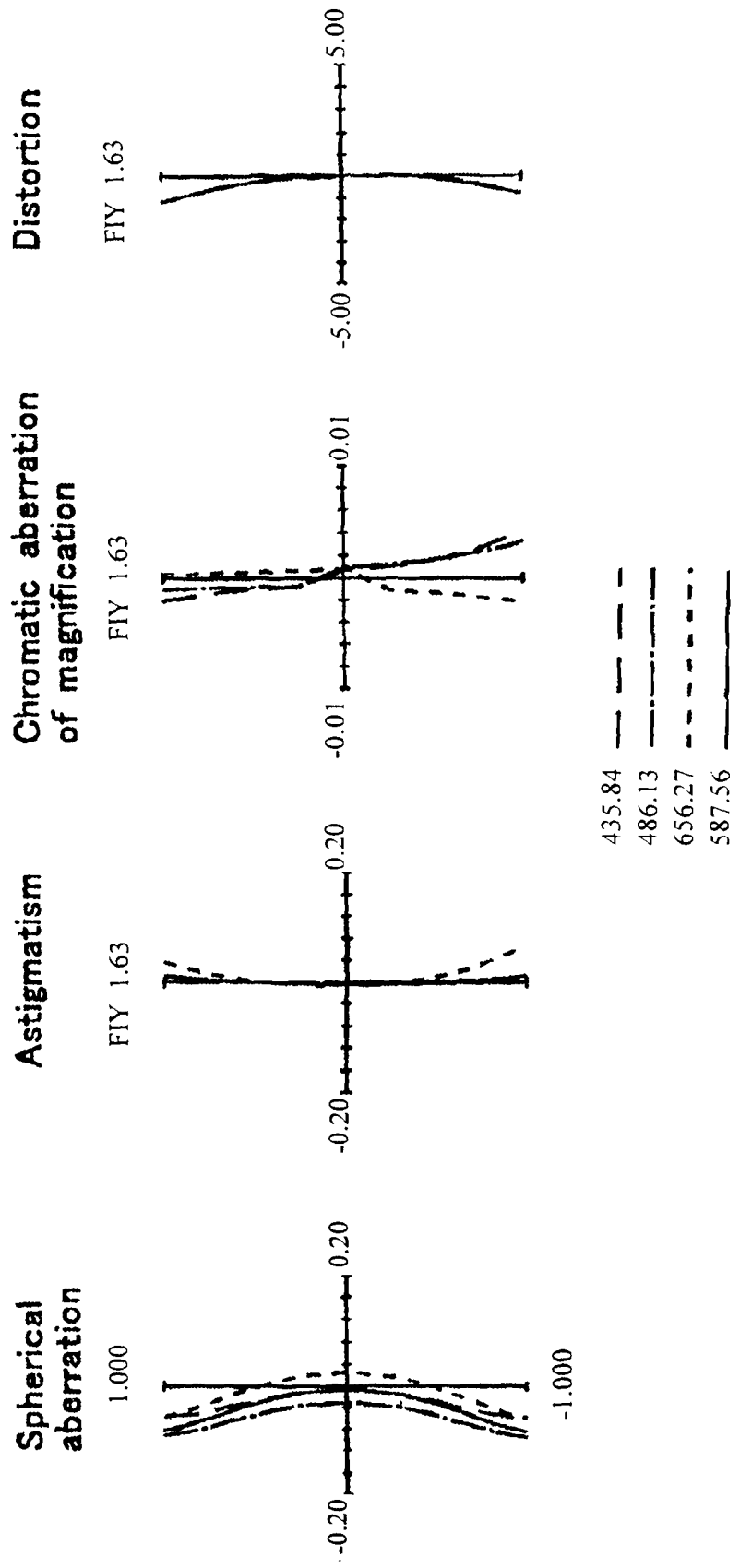

Aberration diagrams of this example similar to FIGS. 9(a), 9(b) and 9(c) corresponding to FIGS. 4(a), 4(b) and 4(c) are presented in FIGS. 12(a), 12(b) and 12(c).

Figure 5A:
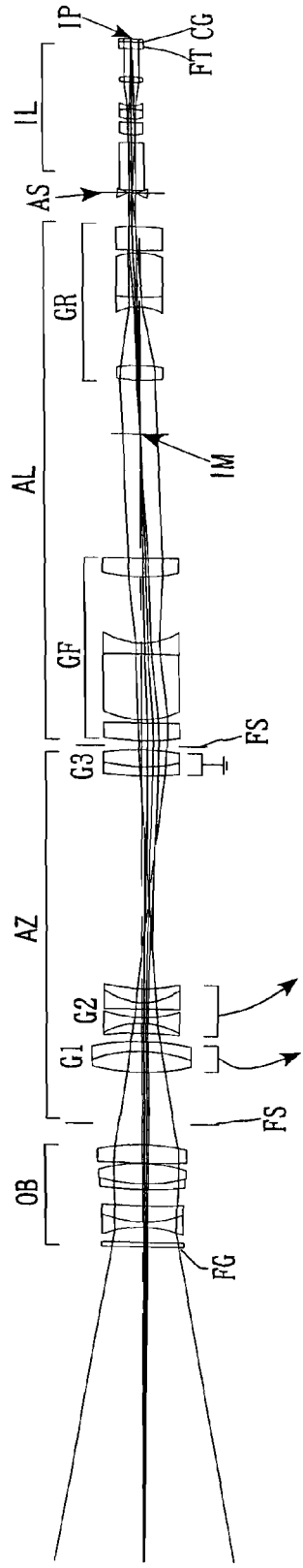
FIG. 5 is illustrative in lens arrangement section of the stereoscopic imaging optical system of Example 4 upon zooming at (a) a low zoom ratio, (b) an intermediate zoom ratio and (c) a high zoom ratio while at a working distance (WD) of 200 mm
Figure 5B:
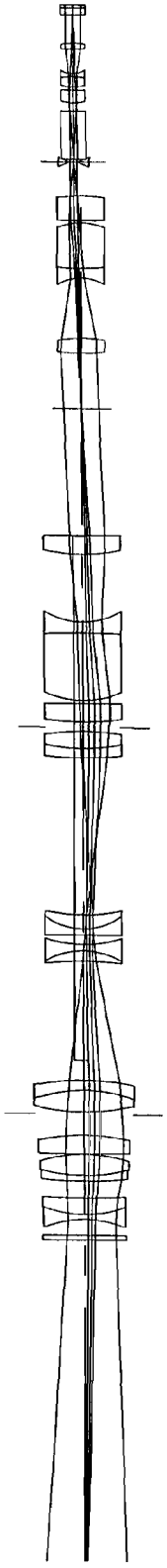
Figure 5C:
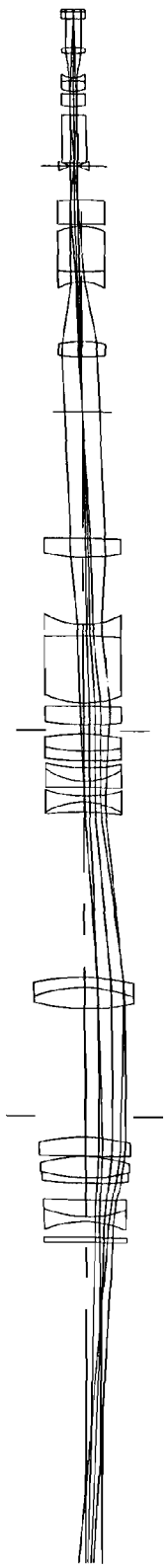

FIG. 5 is illustrative in lens arrangement section of the stereoscopic imaging optical system of Example 4 at (a) a low zoom ratio, (b) an intermediate zoom ratio and (c) a high zoom ratio while at a working distance (WD) of 200 mm, and FIG. 6 is illustrative in lens arrangement section of Example 4 at a low zoom ratio while at (a) WD=200 mm, (b) WD=100 mm and (c) WD=400 mm. For a left-and-right pair of components, only one is shown.

Example 4 is made up of the objective lens optical system OB common to both eyes, the subsequent afocal zoom optical system AZ and afocal relay optical system AL, and the subsequent left-and-right pair of aperture stops AS and imaging optical systems IL. The afocal zoom optical system AZ is made up of a positive first group G1, a negative second group G2 and a positive third group G3, and the afocal relay optical system AL is made up of the positive front group GF and the positive rear group GR with the intermediate image IM held between them. Upon zooming from a low to a high zoom ratio, the first group G1 in the afocal zoom optical system AZ first moves toward the object side and then goes back to the image plane side, and at the high zoom ratio it is positioned more on the image plane side than at the low zoom ratio. The second group G2 moves toward the image plane side while the space between it and the first group G1 grows wide, and the third group G3 remains fixed.

The objective lens optical system OB is made up of a front group consisting of a cemented lens of a double-concave negative lens and a positive meniscus lens convex on its object side, and a rear group consisting of a cemented lens of a negative meniscus lens convex on its object side and a double-convex positive lens, and a double-convex positive lens. By letting out that rear group toward the object side, the WD is kept long. See FIG. 6.

Referring now to the numerical data given later, Surface Nos. 1 and 2 are the end cover glass FG, Surface Nos. 3, 4 and 5 are the cemented lens in the front group in the objective lens optical system OB, Surface Nos. 6, 7 and 8 are the cemented lens in the rear group in the objective lens optical system OB, Surface Nos. 9 and 10 are the double-convex positive lens in the rear group in the objective lens optical system OB, Surface No. 11 is the flare stop FS, and Surface Nos. 12 through 23 are the afocal zoom optical system AZ. The first group G1 in the afocal zoom optical system AZ is made up of a cemented lens of a double-convex positive lens and a negative meniscus lens convex on its image plane side, indicated by Surface Nos. 12, 13 and 14, the second group G2 is made up of a cemented lens of a cemented lens of a positive meniscus lens convex on its image plane side and a double-concave negative lens, indicated by Surface Nos. 15, 16 and 17 and a plano-concave negative lens and a positive meniscus lens convex on its object side, indicated by Surface Nos. 18, 19 and 20, and the third group G3 is made up of a cemented lens of a negative meniscus lens convex on its object side and a double-convex positive lens, indicated by Surface Nos. 21, 22 and 23. Following this, there are the flare stop FS of Surface No. 24 and the afocal relay optical system AL of Surface Nos. 25 through 39. The front group GF in the afocal relay optical system AL is made up of a double-convex positive lens of Surface Nos. 25 and 26 and a cemented lens of a double-convex positive lens and a double-concave negative lens indicated by Surface Nos. 27, 28 and 29, and Surface No. 32 is the intermediate image IM. The rear group GR in the afocal relay optical system AL is made up of a double-convex positive lens of Surface Nos. 33 and 34, a cemented lens of a double-concave negative lens and a double-convex positive lens indicated by Surface Nos. 35, 36 and 37 and a double-convex positive lens of Surface Nos. 38 and 39. And after the aperture stop AS of Surface No. 40, there is the imaging optical system IL of Surface Nos. 43 and 44. The imaging optical system IL is made up of a plane-parallel plate of Surface Nos. 41 and 42, a positive meniscus lens convex on its object side, indicated by Surface Nos. 43 and 44, a cemented lens of a double-convex positive lens and a double-concave negative lens indicated by Surface Nos. 45, 46 and 47, and a double-convex positive lens of Surface Nos. 48 and 49. Following this, there is the optical member (plane-parallel plate) FT of Surface Nos. 50 and 51, after which there is the imaging plane (image plane) IP of Surface No. 54 positioned that has the CCD chip sealing glass CG indicated by Surface Nos. 52 and 53.

It should here be noted that a portion from the aperture stop AS to the imaging plane IP is decentered 3.000 mm in the vertical direction to the optical axis of the objective lens optical system OB, afocal zoom optical system AZ and afocal relay optical system AL.

Figure 13A:
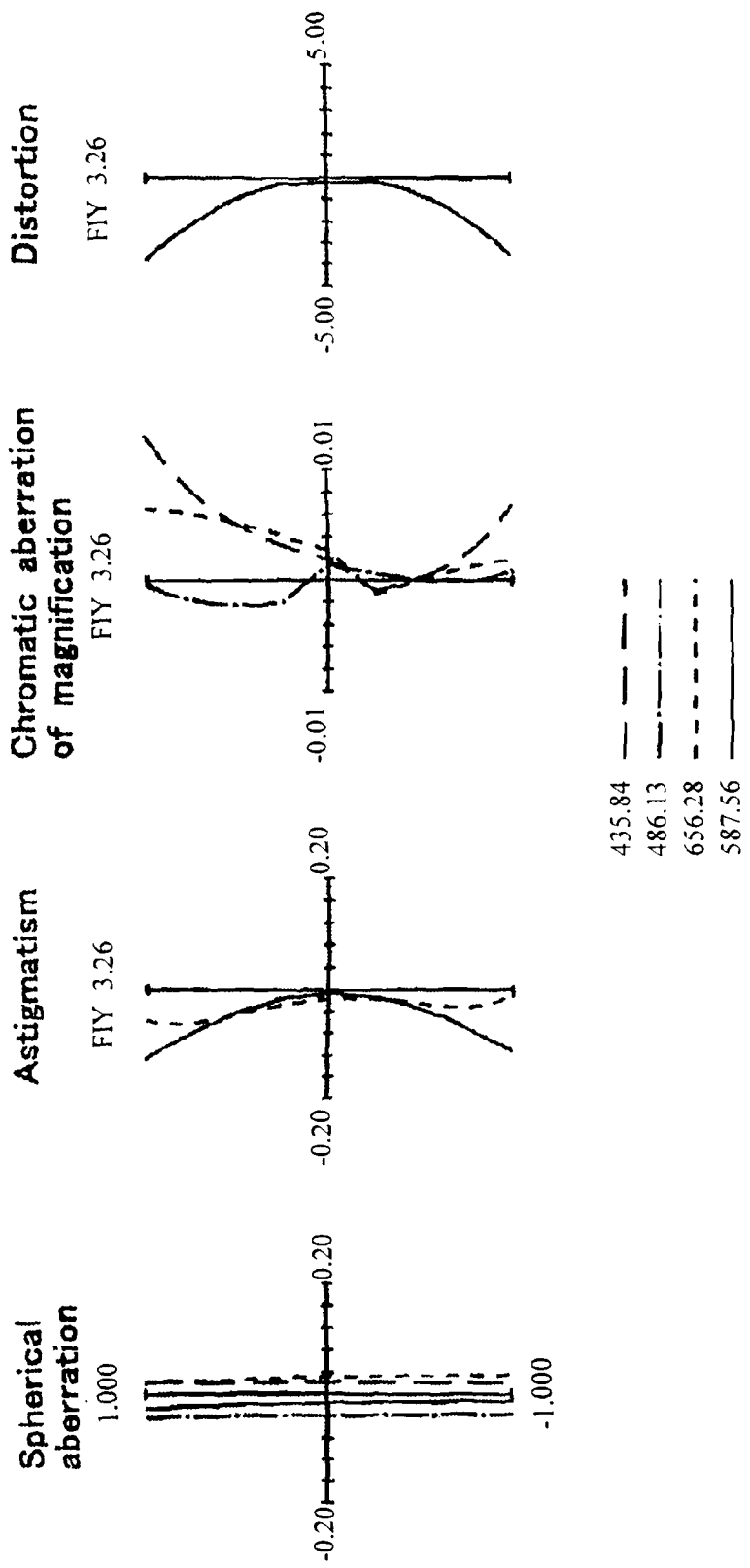
FIG. 13 is indicative of aberrations of Example 4, as in FIGS. 9(a), 9(b) and 9(c) corresponding to FIGS. 5(a), 5(b) and 5(c).
Figure 13B:
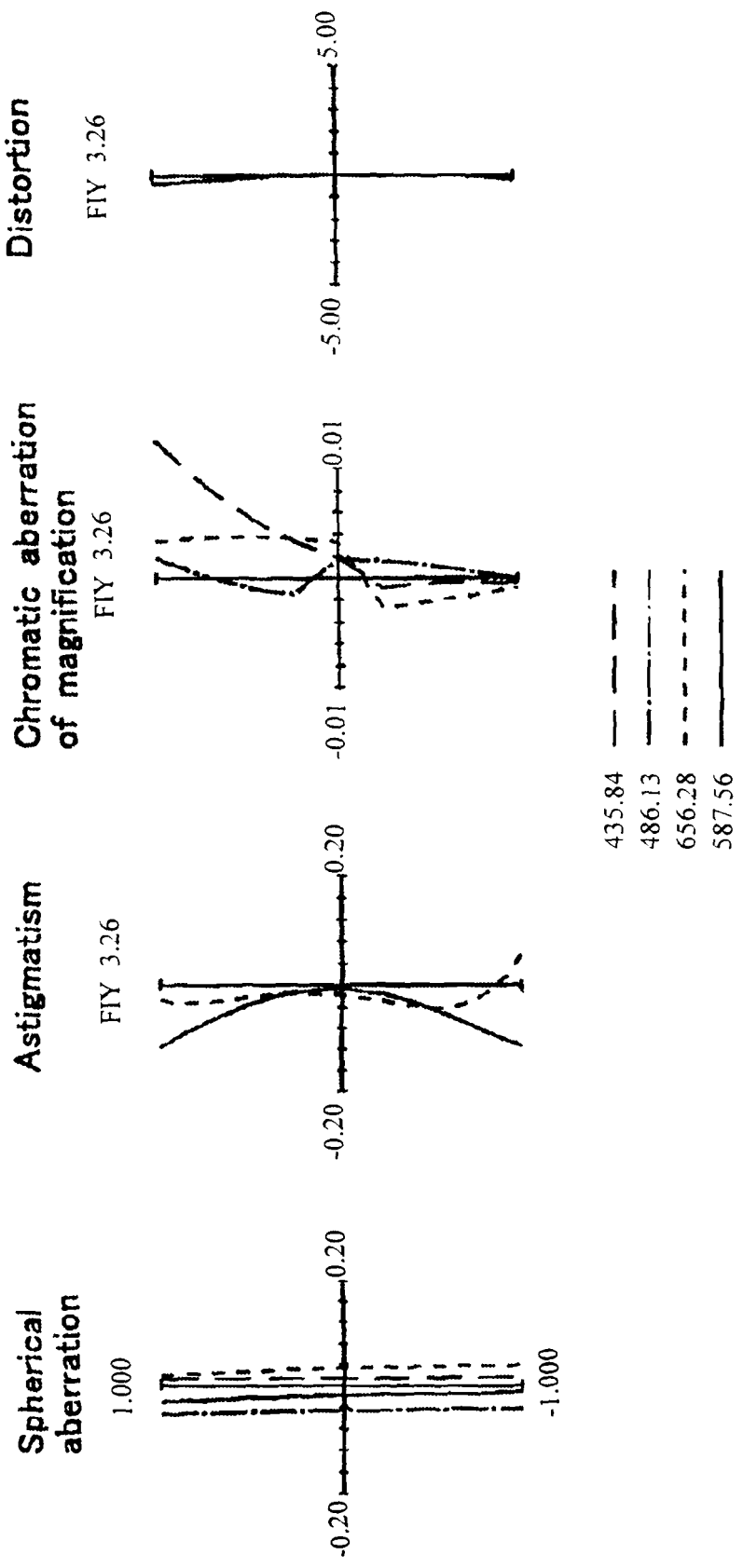
Figure 13C:
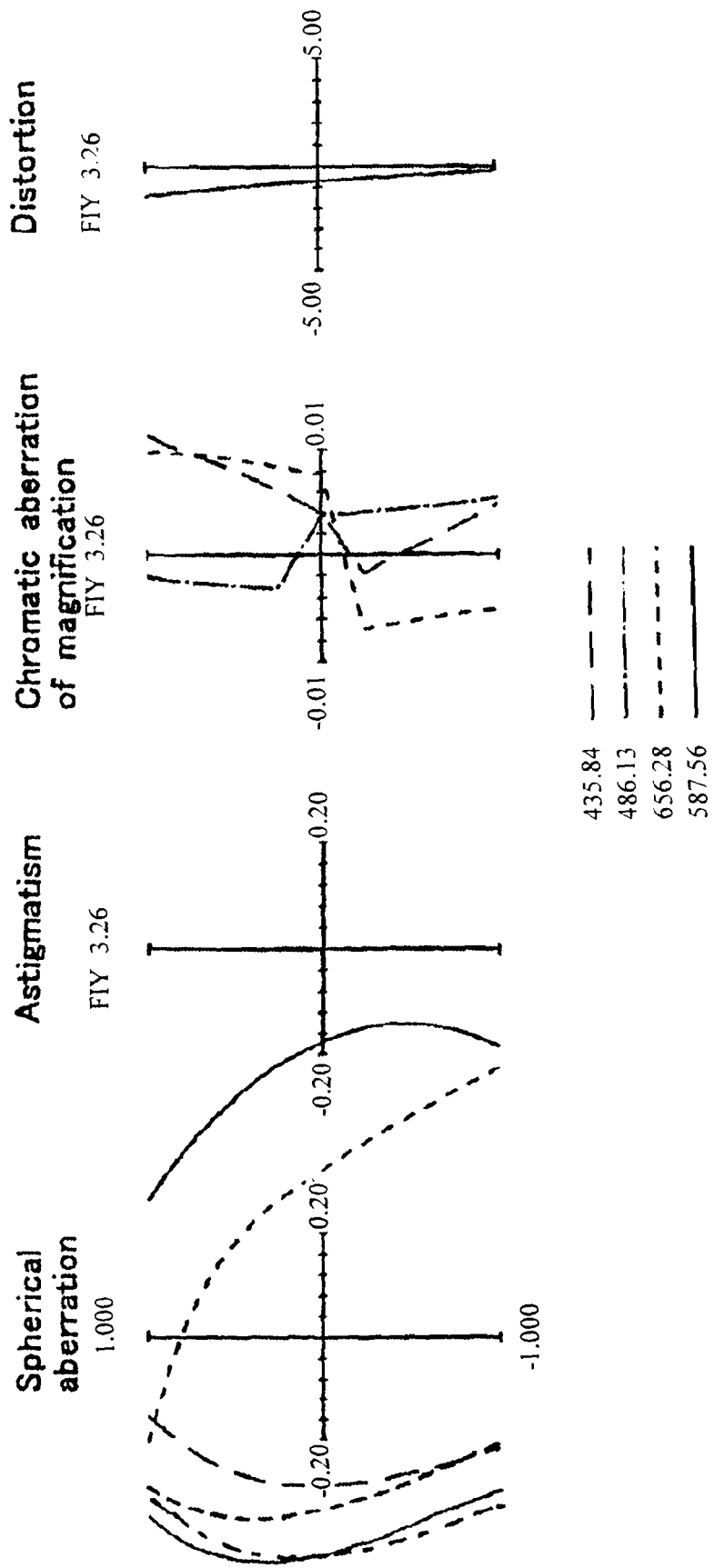
Figure 14C:
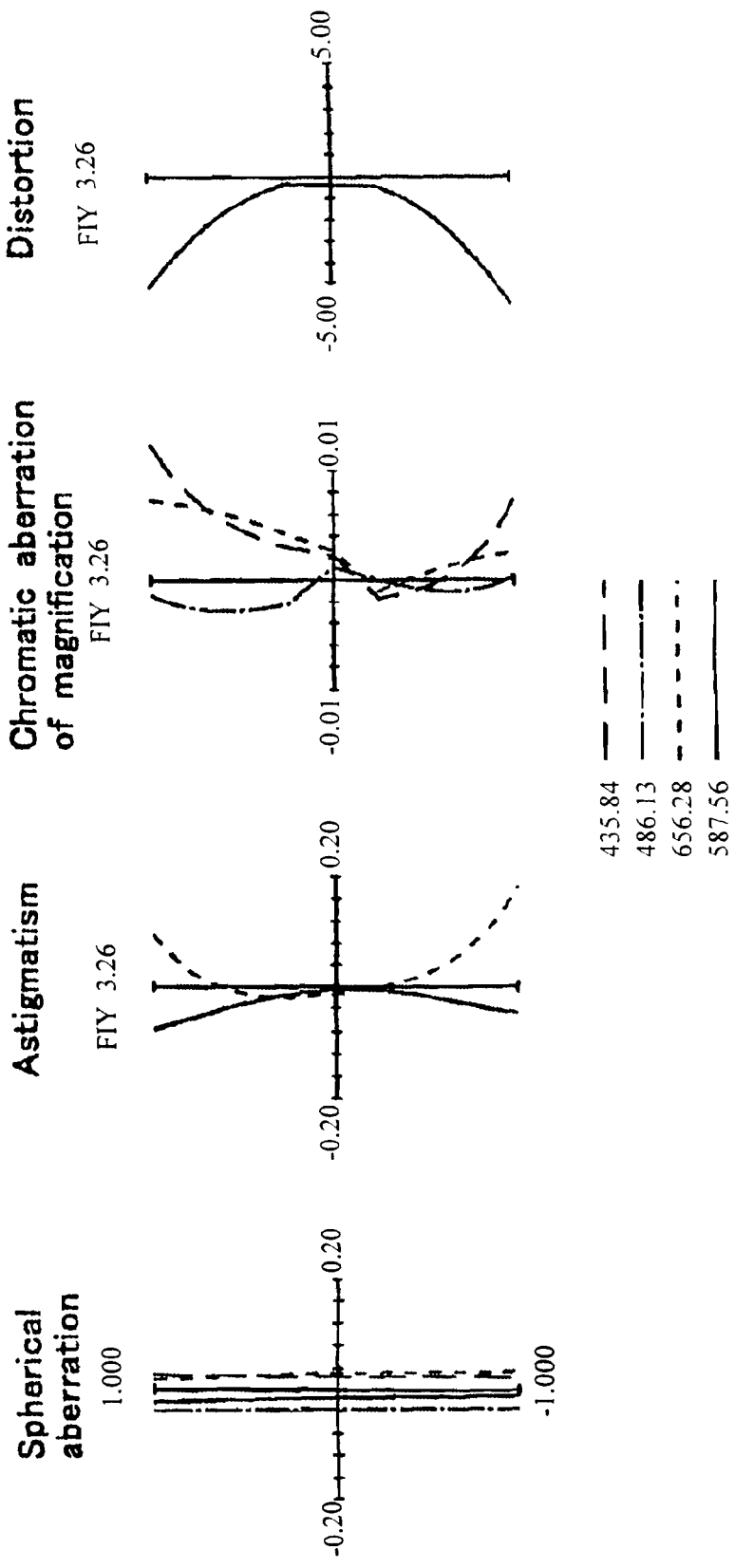
FIG. 14 is indicative of aberrations of Example 4, as in FIGS. 10(a), 10(b) and 10(c) corresponding to FIGS. 6(a), 6(b) and 6(c).

Aberration diagrams of this example are presented in FIGS. 13 and 14. FIGS. 13(a), 13(b) and 13(c), and FIGS. 14(a), 14(b) and 14(c) similar to FIGS. 9(a), 9(b) and 9(c), and FIGS. 10(a), 10(b) and 10(c) are aberration diagrams in the states of FIGS. 5(a), 5(b) and 5(c), and FIGS. 6(a), 6(b) and 6(c), respectively.

FIG. 7 is illustrative in lens arrangement section of the stereoscopic imaging optical system of Example 5 at (a) a low zoom ratio, (b) an intermediate zoom ratio and (c) a high zoom ratio while at a working distance (WD) of 200 mm. For a left-and-right pair of components, only one is shown.

Example 5 is made up of the objective lens optical system OB common to both eyes, the subsequent afocal zoom optical system AZ and afocal relay optical system AL, and the subsequent left-and-right pair of aperture stops AS and imaging optical systems IL. The afocal zoom optical system AZ is made up of a positive first group G1, a negative second group G2 and a positive third group G3, and the afocal relay optical system AL is made up of the positive front group GF and the positive rear group GR with the intermediate image IM held between them. Upon zooming from a low to a high zoom ratio, the first group G1 in the afocal zoom optical system AZ first moves toward the object side and then goes back to the image plane side, and at the high zoom ratio it is positioned more on the image plane side than at the low zoom ratio. The second group G2 moves toward the image plane side while the space between it and the first group G1 grows wide, and the third group G3 remains fixed.

The objective lens optical system OB is made up of a front group consisting of a cemented lens of a double-concave negative lens and a positive meniscus lens convex on its object side, and a rear group consisting of a cemented lens of a negative meniscus lens convex on its object side and a double-convex positive lens, and a double-convex positive lens. By letting out that rear group toward the object side, the WD is kept long.

Referring here to the numerical data given later, Surface Nos. 1 and 2 are the end front cover glass FG, Surface Nos. 3, 4 and 5 are the cemented lens in the front group in the objective lens optical system OB, Surface Nos. 6, 7 and 8 are the cemented lens in the rear group in the objective lens optical system OB, and Surface Nos. 9 and 10 are the double-convex positive lens in the rear group in the objective lens optical system OB. Surface No. 11 is the flare stop FS followed by the afocal zoom optical system AZ of Surface Nos. 12 through 23. The first group in the afocal zoom optical system AZ is made up of a cemented lens of a double-convex positive lens and a negative meniscus lens convex on its image plane side, indicated by Surface Nos. 12, 13 and 14, the second group G2 is made up of a cemented lens of a positive meniscus lens convex on its image plane side and a double-concave negative lens, indicated by Surface Nos. 15, 16 and 17 and a cemented lens of a plano-concave negative lens and a positive meniscus lens convex on its object side, indicated by Surface Nos. 18, 19 and 20, and the third group G3 is made up of a cemented lens of a negative meniscus lens convex on its object side, indicated by Surface Nos. 21, 22 and 23. Following this, there is the flare stop FS of Surface No. 24 followed by the afocal relay optical system AL indicated by Surface Nos. 25 through 39. The front group GF in the afocal relay optical system AL is made up of a double-convex positive lens of Surface Nos. 25 and 26, a cemented lens of a double-convex positive lens and a double-concave negative lens, indicated by Surface Nos. 27, 28 and 29 and a positive meniscus lens convex on its object side, indicated by Surface Nos. 30 and 31, with Surface No. 32 indicative of the intermediate image IM. The rear group GR in the afocal relay optical system AL is made up of a double-convex positive lens of Surface Nos. 33 and 34, a cemented lens of a double-concave negative lens and a double-convex positive lens, indicated by Surface Nos. 35, 36 and 37 and a double-convex positive lens of Surface No. 38 and 39. And after the aperture stop AS of Surface No. 40, there is the imaging optical system IL of Surface No. 41 through 49. The imaging optical system IL is made up of a plane-parallel plate of Surface Nos. 41 and 42, a positive meniscus lens convex on its object side, indicated by Surface Nos. 43 and 44, a cemented lens of a double-convex positive lens and a double-concave negative lens, indicated by Surface Nos. 45, 46 and 47, and a double-convex positive lens of Surface Nos. 48 and 49. Following this, there is the optical member (plane-parallel plate) FT of Surface Nos. 50 and 51 positioned, after which there is the imaging plane (image plane) IP of Surface No. 54 positioned that has the CCD chip sealing glass DG of Surface Nos. 52 and 53.

It should here be noted that a portion from the aperture stop AS to the imaging plane IP is decentered 4.2000 mm in the vertical direction to the optical axis of the objective lens optical system OB, afocal zoom optical system AZ and afocal relay optical system AL.

Figure 15A:
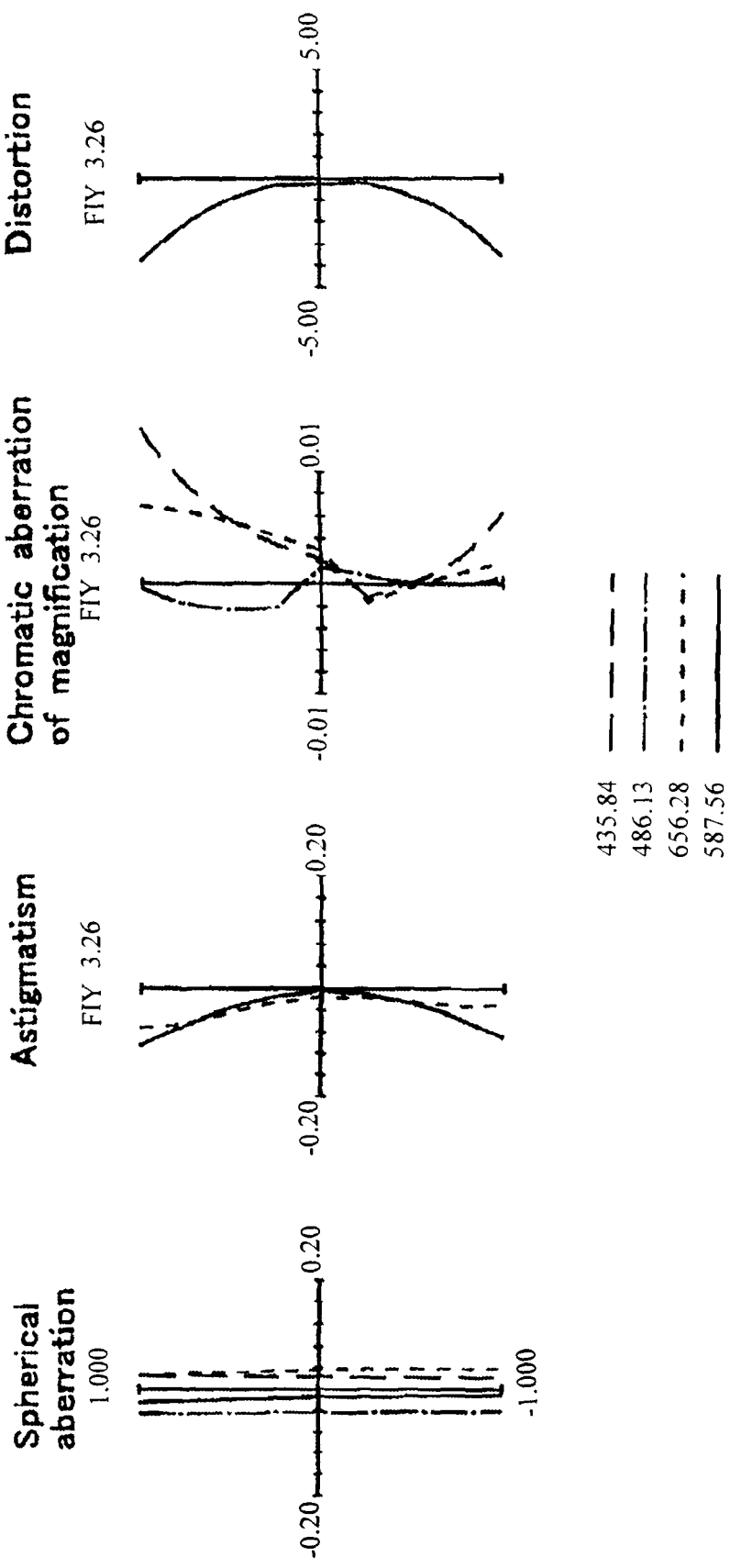
FIG. 15 is indicative of aberrations of Example 5, as in FIGS. 9(a), 9(b) and 9(c) corresponding to FIGS. 7(a), 7(b) and 7(c).

Aberration diagrams of this example similar to FIGS. 13(a), 13(b) and 13(c) corresponding to FIGS. 7(a), 7(b) and 7(c) are presented in FIGS. 15(a), 15(b) and 15(c), respectively.

Figure 8A:
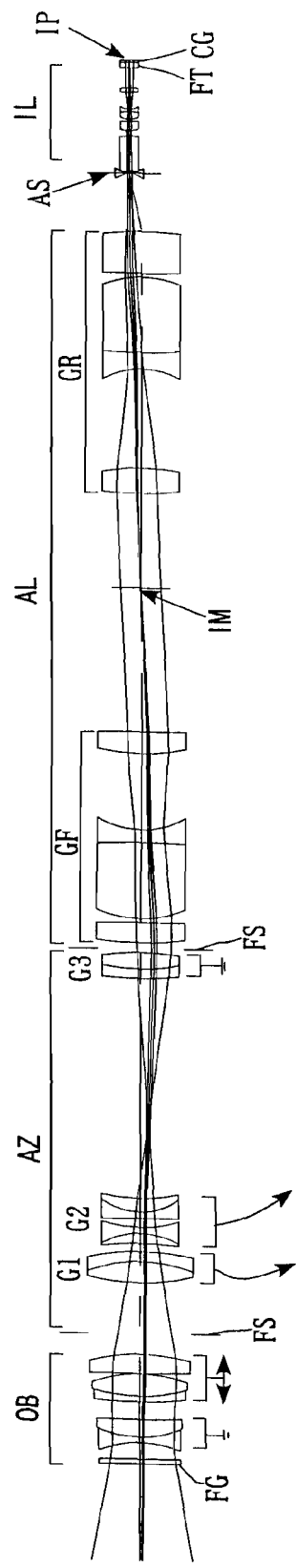
FIG. 8 is illustrative in lens arrangement section of the stereoscopic imaging optical system of Example 6 upon zooming at (a) a low zoom ratio, (b) an intermediate zoom ratio and (c) a high zoom ratio while at a working distance (WD) of 200 mm.
Figure 8B:
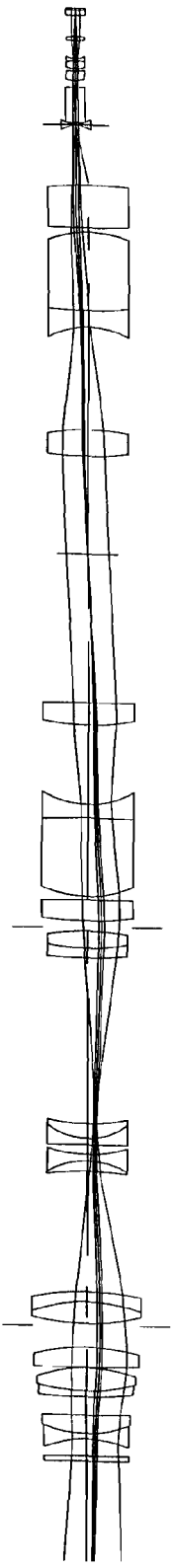
Figure 8C:
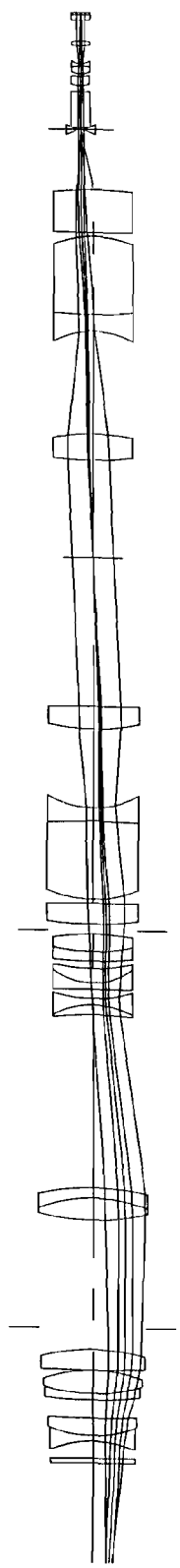

FIG. 8 is illustrative in lens arrangement section of the stereoscopic imaging optical system of Example 6 at (a) a low zoom ratio, (b) an intermediate zoom ratio and (c) a high zoom ratio (c) while at a working distance (WD) of 200 mm. For a left-and-right pair of components, only one is shown.

Example 6 is made up of the objective lens optical system OB common to both eyes, the subsequent afocal zoom optical system AZ and afocal relay optical system AL, and the subsequent left-and-right pair of aperture stops AS and imaging optical systems IL. The afocal zoom optical system AZ is made up of a positive first group G1, a negative second group G2 and a positive third group G3, and the afocal relay optical system AL is made up of the positive front group GF and the positive rear group GR with the intermediate image IM held between them. Upon zooming from a low to a high zoom ratio, the first group G1 in the afocal zoom optical system AZ first moves toward the object side and then goes back to the image plane side, and at the high zoom ratio it is positioned more on the image plane side than at the low zoom ratio. The second group G2 moves toward the image plane side while the space between it and the first group G1 grows wide, and the third group G3 remains fixed.

The objective lens optical system OB is made up of a front group consisting of a cemented lens of a double-concave negative lens and a positive meniscus lens convex on its object side, and a rear group consisting of a cemented lens of a negative meniscus lens convex on its object side and a double-convex positive lens, and a double-convex positive lens. By letting out that rear group toward the object side, the WD is kept long.

Referring now to the numerical data given later, Surface Nos. 1 and 2 are the end cover glass FG, Surface Nos. 3, 4 and 5 are the cemented lens in the front group in the objective lens optical system OB, Surface Nos. 9 and 10 are the double-convex positive lens in the rear group in the objective lens optical system OB, Surface No. 11 is the flare stop FS, and Surface Nos. 12 through 23 are the afocal zoom optical system AZ. The first group G1 in the afocal zoom optical system AZ is made up of a cemented lens of a double-convex positive lens and a negative meniscus lens convex on its image plane side, indicated by Surface Nos. 12, 13 and 14, the second group G2 is made up of a cemented lens of a positive meniscus lens convex on its image plane side and a double-concave negative lens, indicated by Surface Nos. 15, 16 and 17 and a cemented lens of a plano-concave negative lens and a positive meniscus lens convex on its object side, indicated by Surface Nos. 18, 19 and 20, and the third group G3 is made up of a cemented lens of a negative meniscus lens convex on its object side and a double-convex positive lens, indicated by Surface Nos. 21, 22 and 23. Following this, there is the flare stop FS of Surface No. 24 that is followed by the afocal relay optical system AL of Surface Nos. 25 through 39. The front group GF in the afocal relay optical system AL is made up of a double-convex positive lens of Surface Nos. 25 and 26, a cemented lens of a double-convex positive lens and a double-concave negative lens, indicated by Surface Nos. 27, 28 and 29 and a positive meniscus lens convex on its object side, indicated by Surface Nos. 30 and 31, and Surface No. 32 is the intermediate image IM. The rear group GR in the afocal relay optical system AL is made up of a double-convex positive lens of Surface Nos. 33 and 34, a cemented lens of a double-concave negative lens and a double-convex positive lens, indicated by Surface Nos. 35, 36 and 37 and a double-convex positive lens of Surface Nos. 38 and 39. After the aperture stop AS of Surface No. 40, there is the imaging optical system IL of Surface Nos. 41 through 49. The imaging optical system IL is made up of a plane-parallel plate of Surface Nos. 41 and 42, a positive meniscus lens convex on its object side, indicated by Surface Nos. 43 and 44, a cemented lens of a double-convex positive lens and a double-concave negative lens indicated by Surface Nos. 45, 46 and 47, and a double-convex positive lens of Surface Nos. 48 and 49. After this, there is the optical member (plane-parallel plate) FT of Surface Nos. 50 and 51 positioned, after which the imaging plane (image plane) IP of Surface No. 54 positioned that has the CCD chip sealing glass CG of Surface Nos. 52 and 53.

It should here be noted that a portion from the aperture stop AS to the imaging plane IP is decentered 5.0000 mm in the vertical direction to the optical axis of the objective lens optical system OB, afocal zoom optical system AZ and afocal relay optical system AL.

Figure 16A:
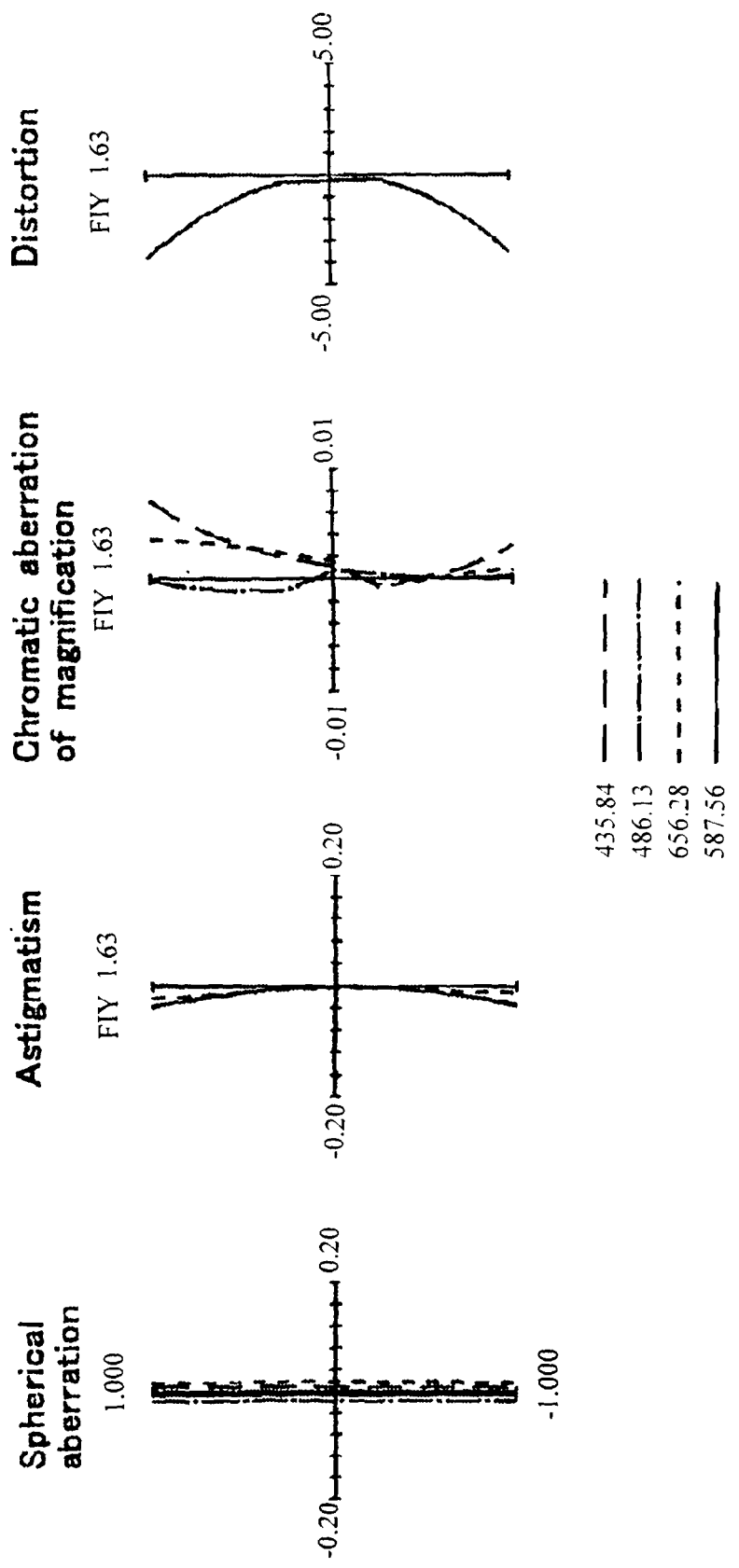
FIG. 16 is indicative of aberrations of Example 6, as in FIGS. 9(a), 9(b) and 9(c) corresponding to FIGS. 8(a), 8(b) and 8(c).
Figure 16C:
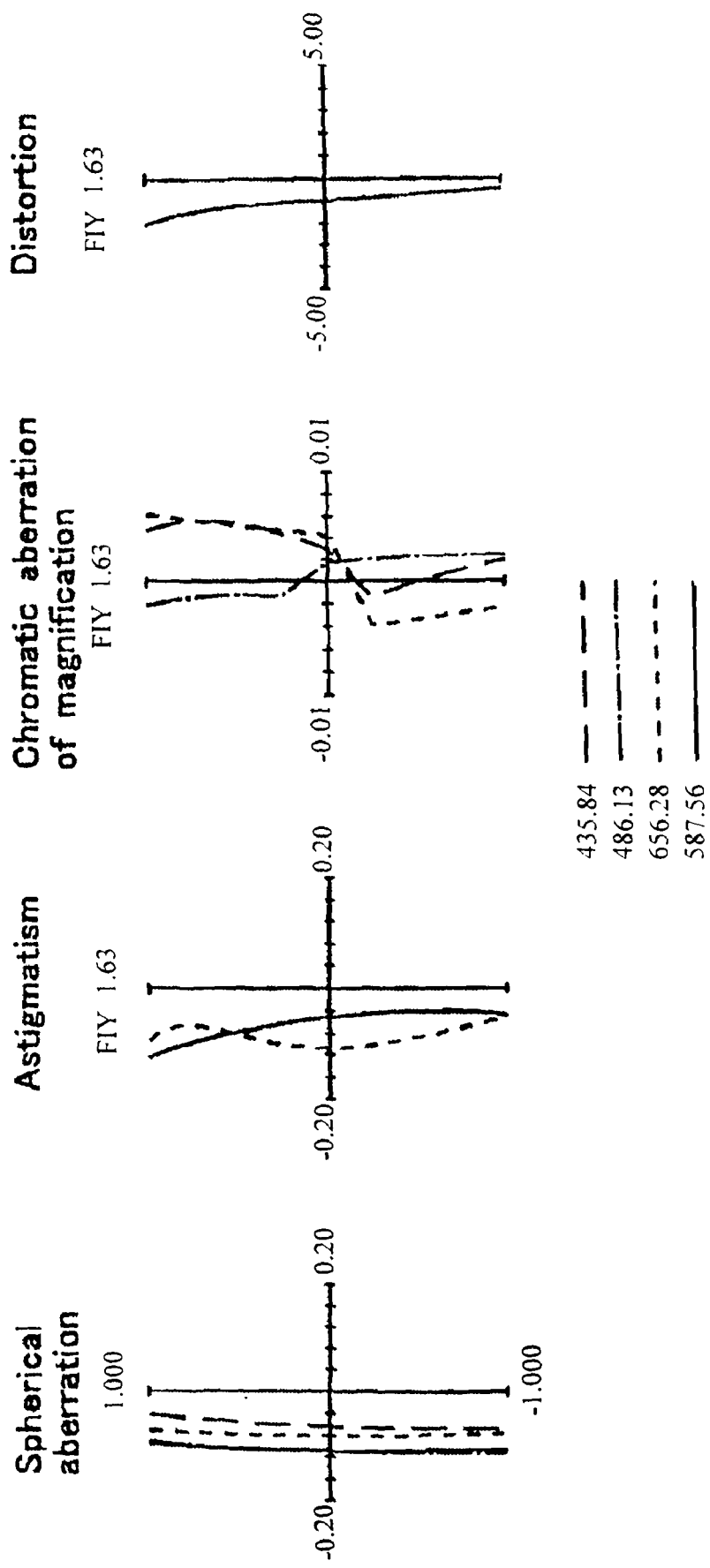
Figure 19A:
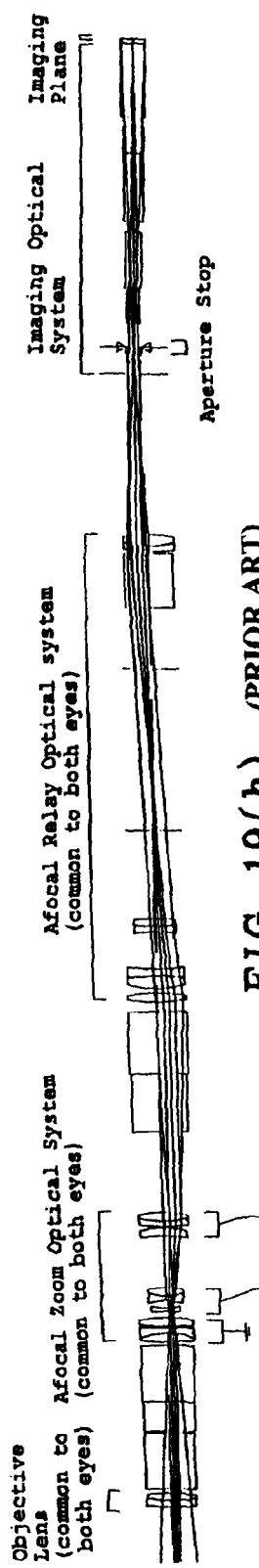
FIG. 19 is a view that is provided to consider what is constructed of the afocal relay optical system with reference to FIG. 18.
Figure 19B:
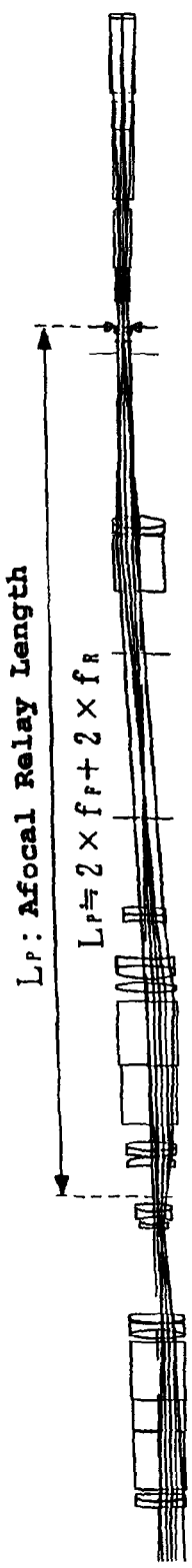
Figure 19C:
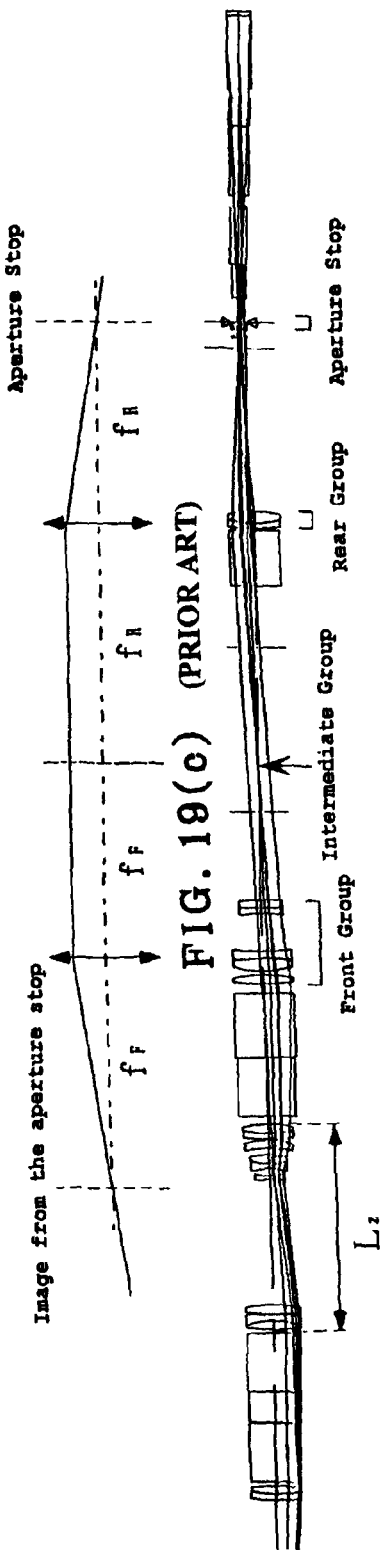

Aberration diagrams of this example similar to FIGS. 13(*a*), 13(*b*) and 13(*c*) corresponding to FIGS. 8(*a*), 8(*b*) and 8(*c*) are presented in FIGS. 16(*a*), 16(*b*) and 16(*c*), respectively.

Set out below are the numerical data on Examples 1 through 6. In the following, "LM", "SM", "HM", "WD" and "MG" are indicative of a low zoom ratio end, an intermediate magnification, a high zoom ratio end, a working distance and a magnification, respectively, with "INF" indicative of infinity.

Example 1

| No | r | d | nd | vd |
|---|---|---|---|---|
| Object plane | INF | Variable | | |
| 1 | INF | 4.0000 | 1.76820 | 71.79 |
| 2 | INF | 7.0000 | | |
| 3 | −47.7464 | 2.5000 | 1.72000 | 43.69 |
| 4 | 48.1827 | 6.5429 | 1.84666 | 23.78 |
| 5 | 308.9917 | Variable | | |
| 6 | 172.9869 | 3.0000 | 1.84666 | 23.78 |
| 7 | 74.8421 | 10.9301 | 1.49700 | 81.54 |
| 8 | −55.6530 | 0.2000 | | |
| 9 | 315.9099 | 5.6845 | 1.51742 | 52.43 |
| 10 | −145.5527 | Variable | | |
| 11 | 66.0435 | 2.5000 | 1.48749 | 70.23 |
| 12 | −125.8197 | 0.2000 | | |
| 13 | 37.1012 | 3.0000 | 1.48749 | 70.23 |
| 14 | −354.0446 | 1.5000 | 1.80100 | 34.97 |
| 15 | 71.3269 | Variable | | |
| 16 | −46.8052 | 1.5000 | 1.77250 | 49.60 |
| 17 | −128.2160 | 1.1726 | | |
| 18 | −70.1821 | 1.2000 | 1.51633 | 64.14 |
| 19 | 10.1313 | 1.9281 | 1.84666 | 23.78 |
| 20 | 13.4863 | Variable | | |
| 21(Stop) | INF | 2.8376 | | |
| 22 | 17.4515 | 2.0000 | 1.62004 | 36.26 |
| 23 | −52.4479 | 0.2000 | | |
| 24 | 159.5462 | 1.2000 | 1.80100 | 34.97 |
| 25 | 9.1524 | 2.0000 | 1.48749 | 70.23 |
| 26 | −47.5162 | Variable | | |
| 27 | −17.4646 | 1.2000 | 1.64769 | 33.79 |
| 28 | 33.2918 | 2.5000 | 1.88300 | 40.76 |
| 29 | −19.2472 | Variable | | |
| 30 | INF | 4.4436 | 1.54771 | 62.84 |
| 31 | INF | 1.9010 | | |
| 32 | INF | 1.9010 | 1.51633 | 64.14 |
| 33 | INF | 0.0001 | | |
| Image plane | INF | | | |

| Variable spaces | | | | | |
|---|---|---|---|---|---|
| No | LM | LM | LM | SM | SM |
| MG | −0.055 | −0.086 | −0.032 | −0.134 | −0.210 |
| d0 WD | 200.00000 | 100.00000 | 400.00000 | 200.00000 | 100.00000 |
| d5 | 7.46760 | 16.31128 | 0.94639 | 7.46760 | 16.31128 |
| d10 | 11.00000 | 2.15632 | 17.52121 | 11.00000 | 2.15632 |
| d15 | 2.00187 | 2.00187 | 2.00187 | 24.39575 | 24.39575 |
| d20 | 42.83668 | 42.83668 | 42.83668 | 20.44279 | 20.44279 |
| d26 | 11.97120 | 11.97120 | 11.97120 | 7.57992 | 7.57992 |
| d29 | 20.26873 | 20.26873 | 20.26873 | 24.66000 | 24.66000 |

| No | SM | HM | HM | HM |
|---|---|---|---|---|
| MG | −0.077 | −0.327 | −0.514 | −0.189 |
| d0 WD | 400.00000 | 200.00000 | 100.00000 | 400.00000 |
| d5 | 0.94639 | 7.46760 | 16.31128 | 0.94639 |
| d10 | 17.52121 | 11.00000 | 2.15632 | 17.52121 |
| d15 | 24.39575 | 41.05094 | 41.05094 | 41.05094 |
| d20 | 20.44279 | 3.78764 | 3.78764 | 3.78764 |
| d26 | 7.57992 | 19.61868 | 19.61868 | 19.61868 |
| d29 | 24.66000 | 12.62123 | 12.62123 | 12.62123 |

Example 2

| No | r | d | nd | vd |
|---|---|---|---|---|
| Object plane | INF | Variable | | |
| 1 | INF | 5.0000 | 1.76820 | 71.79 |
| 2 | INF | 8.0000 | | |
| 3 | −38.1697 | 3.8657 | 1.54072 | 47.23 |
| 4 | 45.3481 | 8.0000 | 1.84666 | 23.78 |
| 5 | 106.5783 | Variable | | |
| 6 | 339.2797 | 7.0000 | 1.62004 | 36.26 |
| 7 | −86.2856 | 0.2000 | | |
| 8 | 93.2957 | 4.0000 | 1.84666 | 23.78 |
| 9 | 47.5470 | 10.0000 | 1.49700 | 81.54 |
| 10 | −115.8492 | Variable | | |
| 11 | 61.5057 | 2.8000 | 1.48749 | 70.23 |
| 12 | −174.8837 | 0.2000 | | |
| 13 | 34.5084 | 3.2000 | 1.48749 | 70.23 |
| 14 | −3043.1666 | 1.5000 | 1.80100 | 34.97 |
| 15 | 60.8400 | Variable | | |
| 16 | 59.9528 | 1.5000 | 1.77250 | 49.60 |
| 17 | 49.6343 | 2.0000 | | |
| 18 | −28.6883 | 1.2000 | 1.51633 | 64.14 |
| 19 | 11.0106 | 1.8836 | 1.84666 | 23.78 |
| 20 | 14.7361 | Variable | | |
| 21(Stop) | INF | 1.9833 | | |
| 22 | 62.8650 | 2.0000 | 1.62004 | 36.26 |
| 23 | −36.6853 | 0.2000 | | |
| 24 | 70.4137 | 1.2000 | 1.80100 | 34.97 |
| 25 | 12.4512 | 2.0000 | 1.48749 | 70.23 |
| 26 | −26.3168 | Variable | | |
| 27 | −12.3601 | 1.2000 | 1.64769 | 33.79 |
| 28 | 26.8585 | 2.5000 | 1.88300 | 40.76 |
| 29 | −15.8201 | Variable | | |

-continued

| | | | | | |
|---|---|---|---|---|---|
| 30 | INF | 4.4436 | 1.54771 | 62.84 | |
| 31 | INF | 1.9010 | | | |
| 32 | INF | 1.9010 | 1.51633 | 64.14 | |
| 33 | INF | 0.0000 | | | |
| Image plane | INF | | | | |

Variable spaces

| No | LM | LM | LM | SM | SM |
|---|---|---|---|---|---|
| MG | −0.055 | −0.087 | −0.032 | −0.135 | −0.212 |
| d0 WD | 200.00000 | 100.00000 | 400.00000 | 200.00000 | 100.00000 |
| d5 | 9.11025 | 17.42919 | 2.93502 | 9.11025 | 17.42919 |
| d10 | 10.00000 | 1.68106 | 16.17523 | 10.00000 | 1.68106 |
| d15 | 1.98945 | 1.98945 | 1.98945 | 24.84908 | 24.84908 |
| d20 | 43.74026 | 43.74026 | 43.74026 | 20.88063 | 20.88063 |
| d26 | 12.12887 | 12.12887 | 12.12887 | 7.65301 | 7.65301 |
| d29 | 20.50251 | 20.50251 | 20.50251 | 24.97840 | 24.97840 |

| No | SM | HM | HM | HM | |
|---|---|---|---|---|---|
| MG | −0.079 | −0.332 | −0.519 | −0.193 | |
| d0 WD | 400.00000 | 200.00000 | 100.00000 | 400.00000 | |
| d5 | 2.93502 | 9.11025 | 17.42919 | 2.93502 | |
| d10 | 16.17523 | 10.00000 | 1.68106 | 16.17523 | |
| d15 | 24.84908 | 41.47434 | 41.47434 | 41.47434 | |
| d20 | 20.88063 | 4.25541 | 4.25541 | 4.25541 | |
| d26 | 7.65301 | 19.95077 | 19.95077 | 19.95077 | |
| d29 | 24.97840 | 12.68060 | 12.68060 | 12.68060 | |

Example 3

| No | r | d | nd | vd |
|---|---|---|---|---|
| Object plane | INF | Variable | | |
| 1 | INF | 2.0000 | 1.76820 | 71.79 |
| 2 | INF | 4.0000 | | |
| 3 | −38.9866 | 2.3000 | 1.72000 | 43.69 |
| 4 | 30.2094 | 5.0000 | 1.84666 | 23.78 |
| 5 | 141.4871 | Variable | | |
| 6 | 844.4155 | 2.4000 | 1.76182 | 26.52 |
| 7 | 42.8249 | 5.0000 | 1.49700 | 81.54 |
| 8 | −207.2773 | 0.2000 | | |
| 9 | 143.0459 | 5.0000 | 1.78800 | 47.37 |
| 10 | −53.0139 | Variable | | |
| 11 | 301.6916 | 2.0000 | 1.69680 | 55.53 |
| 12 | −79.7609 | 0.2000 | | |
| 13 | 25.2283 | 2.2000 | 1.69680 | 55.53 |
| 14 | 806.7235 | 1.5000 | 1.84666 | 23.78 |
| 15 | 46.6578 | Variable | | |
| 16 | 18.5970 | 1.1777 | 1.77250 | 49.60 |
| 17 | 11.6121 | 1.1873 | | |
| 18 | −12.3112 | 1.0000 | 1.51633 | 64.14 |
| 19 | 8.2966 | 1.6168 | 1.84666 | 23.78 |
| 20 | 14.6164 | Variable | | |
| 21(Stop) | INF | 2.1998 | | |
| 22 | −11.3858 | 2.9089 | 1.51742 | 52.43 |
| 23 | −11.2501 | 0.2000 | | |
| 24 | 18.8215 | 3.5185 | 1.48749 | 70.23 |
| 25 | −7.3570 | 1.0000 | 1.80100 | 34.97 |
| 26 | −13.2065 | Variable | | |
| 27 | −99.2269 | 1.0000 | 1.72825 | 28.46 |
| 28 | 46.8422 | 2.6666 | 1.69350 | 53.20 |
| 29 | −24.0466 | Variable | | |
| 30 | INF | 2.4173 | 1.54771 | 62.84 |
| 31 | INF | 1.0342 | | |
| 32 | INF | 1.0342 | 1.51633 | 64.14 |
| 33 | INF | 0.0000 | | |
| Image plane | INF | | | |

-continued

Variable spaces

| No | LM | LM | LM | SM | SM |
|---|---|---|---|---|---|
| MG | −0.030 | −0.050 | −0.017 | −0.074 | −0.122 |
| d0 WD | 200.00000 | 100.00000 | 400.00000 | 200.00000 | 100.00000 |
| d5 | 5.73770 | 11.75525 | 1.64246 | 5.73770 | 11.75525 |
| d10 | 8.00000 | 1.98245 | 12.09524 | 8.00000 | 1.98245 |
| d15 | 2.01300 | 2.01300 | 2.01300 | 15.00261 | 15.00261 |
| d20 | 26.82074 | 26.82074 | 26.82074 | 13.83112 | 13.83112 |
| d26 | 7.81433 | 7.81433 | 7.81433 | 5.24581 | 5.24581 |
| d29 | 11.96285 | 11.96285 | 11.96285 | 14.53136 | 14.53136 |

| No | SM | HM | HM | HM |
|---|---|---|---|---|
| MG | −0.041 | −0.181 | −0.298 | −0.101 |
| d0 WD | 400.00000 | 200.00000 | 100.00000 | 400.00000 |
| d5 | 1.64246 | 5.73770 | 11.75525 | 1.64246 |
| d10 | 12.09524 | 8.00000 | 1.98245 | 12.09524 |
| d15 | 15.00261 | 23.77576 | 23.77576 | 23.77576 |
| d20 | 13.83112 | 5.05798 | 5.05798 | 5.05798 |
| d26 | 5.24581 | 12.50829 | 12.50829 | 12.50829 |
| d29 | 14.53136 | 7.26888 | 7.26888 | 7.26888 |

Example 4

| No | r | d | nd | vd |
|---|---|---|---|---|
| Object plane | INF | Variable | | |
| 1 | INF | 2.0000 | 1.76820 | 71.79 |
| 2 | INF | 7.0000 | | |
| 3 | −44.6801 | 2.3000 | 1.72000 | 43.69 |
| 4 | 48.3881 | 7.1082 | 1.84666 | 23.78 |
| 5 | 318.5902 | Variable | | |
| 6 | 169.9400 | 2.5000 | 1.84666 | 23.78 |
| 7 | 73.2558 | 9.2642 | 1.49700 | 81.54 |
| 8 | −62.6930 | 0.2000 | | |
| 9 | 725.0873 | 8.2212 | 1.51742 | 52.43 |
| 10 | −85.1320 | Variable | | |
| 11 | INF | Variable | | |
| 12 | 91.2516 | 9.2286 | 1.48749 | 70.21 |
| 13 | −61.8721 | 4.3429 | 1.85026 | 32.29 |
| 14 | −104.6601 | Variable | | |
| 15 | −134.4576 | 4.3429 | 1.69895 | 30.12 |
| 16 | −33.1197 | 2.7143 | 1.77250 | 49.60 |
| 17 | 54.0143 | 3.9086 | | |
| 18 | INF | 2.7143 | 1.60311 | 60.70 |
| 19 | 27.3627 | 5.9714 | 1.83400 | 37.17 |
| 20 | 73.1826 | Variable | | |
| 21 | 151.1097 | 4.0714 | 1.74000 | 31.71 |
| 22 | 76.1764 | 7.3286 | 1.48749 | 70.21 |
| 23 | −105.6481 | 1.5079 | | |
| 24 | INF | 2.4576 | | |
| 25 | 122.1364 | 7.7156 | 1.72916 | 54.68 |
| 26 | −8389.0707 | 1.4570 | | |
| 27 | 40.0790 | 28.5137 | 1.49700 | 81.54 |
| 28 | −342.3266 | 4.7763 | 1.80100 | 34.97 |
| 29 | 32.3499 | 28.5252 | | |
| 30 | 75.4974 | 8.0869 | 1.78800 | 47.37 |
| 31 | 157700.0000 | 53.9326 | | |
| 32 | INF | 23.7196 | | |
| 33 | 78.3905 | 6.4649 | 1.72916 | 54.68 |
| 34 | −54.0423 | 25.5253 | | |
| 35 | −19.9811 | 4.1242 | 1.80100 | 34.97 |
| 36 | 100.1661 | 19.1718 | 1.49700 | 81.54 |
| 37 | −26.2721 | 1.0032 | | |
| 38 | 254.8381 | 10.2547 | 1.72916 | 54.68 |
| 39 | −93.3311 | 14.1071 | | |
| 40(Stop) | INF | 1.1905 | | |
| 41 | INF | 19.0476 | 1.80610 | 40.92 |
| 42 | INF | 3.4524 | | |
| 43 | 17.9187 | 5.1372 | 1.77250 | 49.60 |
| 44 | 99.2240 | 1.2383 | | |
| 45 | 13.9102 | 4.2921 | 1.49700 | 81.54 |

-continued

| | | | | |
|---|---|---|---|---|
| 46 | −32.3689 | 1.1636 | 1.80100 | 34.97 |
| 47 | 10.0010 | 9.8698 | | |
| 48 | 33.7316 | 2.4441 | 1.72916 | 54.68 |
| 49 | −33.7316 | 11.4922 | | |
| 50 | INF | 2.9762 | 1.51633 | 64.14 |
| 51 | INF | 0.0060 | | |
| 52 | INF | 1.1905 | 1.61350 | 50.20 |
| 53 | INF | 0.0017 | | |
| Image plane | INF | | | |

Variable spaces

| No | LM | LM | LM | SM | SM |
|---|---|---|---|---|---|
| MG | 0.067 | 0.106 | 0.038 | 0.161 | 0.256 |
| d0 WD | 200.00000 | 100.00000 | 400.00000 | 200.00000 | 100.00000 |
| d5 | 7.40545 | 15.60189 | 1.47307 | 7.40545 | 15.60189 |
| d10 | 9.00000 | 0.80356 | 14.93238 | 9.00000 | 0.80356 |
| d11 | 22.81629 | 22.81629 | 22.81629 | 1.06671 | 1.06671 |
| d14 | 3.68326 | 3.68326 | 3.68326 | 51.18641 | 51.18641 |
| d20 | 94.44926 | 94.44926 | 94.44926 | 68.69660 | 68.69660 |

| No | SM | HM | HM | HM |
|---|---|---|---|---|
| MG | 0.093 | 0.402 | 0.638 | 0.231 |
| d0 WD | 400.00000 | 200.00000 | 100.00000 | 400.00000 |
| d5 | 1.47307 | 7.40545 | 15.60189 | 1.47307 |
| d10 | 14.93238 | 9.00000 | 0.80356 | 14.93238 |
| d11 | 1.06671 | 46.49843 | 46.49843 | 46.49843 |
| d14 | 51.18641 | 71.35429 | 71.35429 | 71.35429 |
| d20 | 68.69660 | 3.09545 | 3.09545 | 3.09545 |

Example 5

| No | r | d | nd | vd |
|---|---|---|---|---|
| Object plane | INF | Variable | | |
| 1 | INF | 2.0000 | 1.76820 | 71.79 |
| 2 | INF | 7.0000 | | |
| 3 | −44.6801 | 2.3000 | 1.72000 | 43.69 |
| 4 | 48.3881 | 7.1082 | 1.84666 | 23.78 |
| 5 | 318.5902 | Variable | | |
| 6 | 169.9400 | 2.5000 | 1.84666 | 23.78 |
| 7 | 73.2558 | 9.2642 | 1.49700 | 81.54 |
| 8 | −62.6930 | 0.2000 | | |
| 9 | 725.0873 | 8.2212 | 1.51742 | 52.43 |
| 10 | −85.1320 | Variable | | |
| 11 | INF | Variable | | |
| 12 | 91.2516 | 9.2286 | 1.48749 | 70.21 |
| 13 | −61.8721 | 4.3429 | 1.85026 | 32.29 |
| 14 | −104.6601 | Variable | | |
| 15 | −134.4576 | 4.3429 | 1.69895 | 30.12 |
| 16 | −33.1197 | 2.7143 | 1.77250 | 49.60 |
| 17 | 54.0143 | 3.9086 | | |
| 18 | INF | 2.7143 | 1.60311 | 60.70 |
| 19 | 27.3627 | 5.9714 | 1.83400 | 37.17 |
| 20 | 73.1826 | Variable | | |
| 21 | 151.1097 | 4.0714 | 1.74000 | 31.71 |
| 22 | 76.1764 | 7.3286 | 1.48749 | 70.21 |
| 23 | −105.6481 | 1.5079 | | |
| 24 | INF | 2.7033 | | |
| 25 | 134.3501 | 8.4871 | 1.72916 | 54.68 |
| 26 | −9227.9778 | 1.6027 | | |
| 27 | 44.0869 | 31.3650 | 1.49700 | 81.54 |
| 28 | −376.5592 | 5.2540 | 1.80100 | 34.97 |
| 29 | 35.5849 | 31.3777 | | |
| 30 | 83.0471 | 8.8956 | 1.78800 | 47.37 |
| 31 | 173400.0000 | 59.3259 | | |
| 32 | INF | 33.2074 | | |
| 33 | 109.7467 | 9.0509 | 1.72916 | 54.68 |
| 34 | −75.6592 | 35.7354 | | |
| 35 | −27.9735 | 5.7738 | 1.80100 | 34.97 |
| 36 | 140.2325 | 26.8406 | 1.49700 | 81.54 |
| 37 | −36.7809 | 1.4044 | | |

-continued

| | | | | |
|---|---|---|---|---|
| 38 | 356.7734 | 14.3566 | 1.72916 | 54.68 |
| 39 | −130.6636 | 19.7500 | | |
| 40(Stop) | INF | 1.5152 | | |
| 41 | INF | 24.2424 | 1.80610 | 40.92 |
| 42 | INF | 4.3939 | | |
| 43 | 22.8057 | 6.5382 | 1.77250 | 49.60 |
| 44 | 126.2851 | 1.5761 | | |
| 45 | 17.7040 | 5.4627 | 1.49700 | 81.54 |
| 46 | −41.1967 | 1.4810 | 1.80100 | 34.97 |
| 47 | 12.7286 | 12.5616 | | |
| 48 | 42.9312 | 3.1107 | 1.72916 | 54.68 |
| 49 | −42.9312 | 14.6265 | | |
| 50 | INF | 3.7879 | 1.51633 | 64.14 |
| 51 | INF | 0.0076 | | |
| 52 | INF | 1.5152 | 1.61350 | 50.20 |
| 53 | INF | 0.0023 | | |
| Image plane | INF | | | |

Variable spaces

| No | LM | LM | LM | SM | SM |
|---|---|---|---|---|---|
| MG | 0.067 | 0.106 | 0.038 | 0.161 | 0.256 |
| d0 WD | 200.00000 | 100.00000 | 400.00000 | 200.00000 | 100.00000 |
| d5 | 7.40545 | 15.60189 | 1.47307 | 7.40545 | 15.60189 |
| d10 | 9.00000 | 0.80356 | 14.93238 | 9.00000 | 0.80356 |
| d11 | 22.81629 | 22.81629 | 22.81629 | 1.06671 | 1.06671 |
| d14 | 3.68326 | 3.68326 | 3.68326 | 51.18641 | 51.18641 |
| d20 | 94.44926 | 94.44926 | 94.44926 | 68.69660 | 68.69660 |

| No | SM | HM | HM | HM |
|---|---|---|---|---|
| MG | 0.093 | 0.402 | 0.638 | 0.231 |
| d0 WD | 400.00000 | 200.00000 | 100.00000 | 400.00000 |
| d5 | 1.47307 | 7.40545 | 15.60189 | 1.47307 |
| d10 | 14.93238 | 9.00000 | 0.80356 | 14.93238 |
| d11 | 1.06671 | 46.49843 | 46.49843 | 46.49843 |
| d14 | 51.18641 | 71.35429 | 71.35429 | 71.35429 |
| d20 | 68.69660 | 3.09545 | 3.09545 | 3.09545 |

Example 6

| No | r | d | nd | vd |
|---|---|---|---|---|
| Object plane | INF | Variable | | |
| 1 | INF | 2.0000 | 1.76820 | 71.79 |
| 2 | INF | 7.0000 | | |
| 3 | −44.6801 | 2.3000 | 1.72000 | 43.69 |
| 4 | 48.3881 | 7.1082 | 1.84666 | 23.78 |
| 5 | 318.5902 | Variable | | |
| 6 | 169.9400 | 2.5000 | 1.84666 | 23.78 |
| 7 | 73.2558 | 9.2642 | 1.49700 | 81.54 |
| 8 | −62.6930 | 0.2000 | | |
| 9 | 725.0873 | 8.2212 | 1.51742 | 52.43 |
| 10 | −85.1320 | Variable | | |
| 11 | INF | Variable | | |
| 12 | 91.2516 | 9.2286 | 1.48749 | 70.21 |
| 13 | −61.8721 | 4.3429 | 1.85026 | 32.29 |
| 14 | −104.6601 | Variable | | |
| 15 | −134.4576 | 4.3429 | 1.69895 | 30.12 |
| 16 | −33.1197 | 2.7143 | 1.77250 | 49.60 |
| 17 | 54.0143 | 3.9086 | | |
| 18 | INF | 2.7143 | 1.60311 | 60.70 |
| 19 | 27.3627 | 5.9714 | 1.83400 | 37.17 |
| 20 | 73.1826 | Variable | | |
| 21 | 151.1097 | 4.0714 | 1.74000 | 31.71 |
| 22 | 76.1764 | 7.3286 | 1.48749 | 70.21 |
| 23 | −105.6481 | 1.5079 | | |
| 24 | INF | 2.8262 | | |
| 25 | 140.4569 | 8.8729 | 1.72916 | 54.68 |
| 26 | −9647.4313 | 1.6755 | | |
| 27 | 46.0908 | 32.7907 | 1.49700 | 81.54 |
| 28 | −393.6755 | 5.4928 | 1.80100 | 34.97 |
| 29 | 37.2024 | 32.8039 | | |

-continued

| | | | | |
|---|---|---|---|---|
| 30 | 86.8220 | 9.3000 | 1.78800 | 47.37 |
| 31 | 181300.0000 | 62.0225 | | |
| 32 | INF | 39.8489 | | |
| 33 | 131.6960 | 10.8611 | 1.72916 | 54.68 |
| 34 | −90.7910 | 42.8825 | | |
| 35 | −33.5682 | 6.9286 | 1.80100 | 34.97 |
| 36 | 168.2790 | 32.2087 | 1.49700 | 81.54 |
| 37 | −44.1371 | 1.6853 | | |
| 38 | 428.1281 | 17.2279 | 1.72916 | 54.68 |
| 39 | −156.7963 | 23.7000 | | |
| 40(Stop) | INF | 0.8696 | | |
| 41 | INF | 13.9130 | 1.80610 | 40.92 |
| 42 | INF | 2.5217 | | |
| 43 | 13.0885 | 3.7524 | 1.77250 | 49.60 |
| 44 | 72.4767 | 0.9045 | | |
| 45 | 10.1605 | 3.1351 | 1.49700 | 81.54 |
| 46 | −23.6433 | 0.8499 | 1.80100 | 34.97 |
| 47 | 7.3051 | 7.2092 | | |
| 48 | 24.6388 | 1.7853 | 1.72916 | 54.68 |
| 49 | −24.6388 | 8.3943 | | |
| 50 | INF | 2.1739 | 1.51633 | 64.14 |
| 51 | INF | 0.0043 | | |
| 52 | INF | 0.8696 | 1.61350 | 50.20 |
| 53 | INF | 0.0014 | | |
| Image plane | INF | | | |

Variable spaces

| No | LM | LM | LM | SM | SM |
|---|---|---|---|---|---|
| MG | 0.033 | 0.053 | 0.019 | 0.081 | 0.128 |
| d0 WD | 200.00000 | 100.00000 | 400.00000 | 200.00000 | 100.00000 |
| d5 | 7.40545 | 15.60189 | 1.47307 | 7.40545 | 15.60189 |
| d10 | 9.00000 | 0.80356 | 14.93238 | 9.00000 | 0.80356 |
| d11 | 22.81629 | 22.81629 | 22.81629 | 1.06671 | 1.06671 |
| d14 | 3.68326 | 3.68326 | 3.68326 | 51.18641 | 51.18641 |
| d20 | 94.44926 | 94.44926 | 94.44926 | 68.69660 | 68.69660 |

| No | SM | HM | HM | HM |
|---|---|---|---|---|
| MG | 0.046 | 0.201 | 0.319 | 0.115 |
| d0 WD | 400.00000 | 200.00000 | 100.00000 | 400.00000 |
| d5 | 1.47307 | 7.40545 | 15.60189 | 1.47307 |
| d10 | 14.93238 | 9.00000 | 0.80356 | 14.93238 |
| d11 | 1.06671 | 46.49843 | 46.49843 | 46.49843 |
| d14 | 51.18641 | 71.35429 | 71.35429 | 71.35429 |
| d20 | 68.69660 | 3.09545 | 3.09545 | 3.09545 |

Tabulated below are the image-side effective F-numbers (Fno) of Examples 1 through 6 and the image height on the imaging device.

| | Example | 1 | 2 | 3 |
|---|---|---|---|---|
| Image-Side Effective Fno | Low zoom ratio end | 8.4 | 8.6 | 4.9 |
| | Intermediate | 8.5 | 8.6 | 4.9 |
| | High zoom ratio end | 8.7 | 9.0 | 5.1 |
| Image Height on the Imaging Device | | 3 | 3 | 1.632 |

| | Example | 4 | 5 | 6 |
|---|---|---|---|---|
| Image-Side Effective Fno | Low zoom ratio end | 10.5 | 10.5 | 10.5 |
| | Intermediate | 10.5 | 10.5 | 10.5 |
| | High zoom ratio end | 10.5 | 10.5 | 10.5 |
| Image Height on the Imaging Device | | 3.264 | 3.264 | 1.632 |

Tabulated below are also the values of the conditions and the values of the conditions' elements in Examples 1 to 6.

| | Example | | | | | |
|---|---|---|---|---|---|---|
| | 1 | 2 | 3 | 4 | 5 | 6 |
| Imaging device size in inch | ⅓ | ⅓ | ⅙ | ⅓ | ⅓ | ⅙ |
| mgrw | −0.456 | −0.437 | −0.417 | — | — | — |
| ΔG4/ΔG2 | 0.196 | 0.198 | 0.216 | — | — | — |
| fF/LZ | — | — | — | 0.736 | 0.809 | 0.486 |
| fF/fR | — | — | — | 1.680 | 1.320 | 1.150 |
| fm/IH | — | — | — | 12.160 | 9.554 | 13.958 |
| ΔG4 | 7.648 | 7.822 | 4.694 | — | — | — |
| ΔG2 | 39.049 | 39.485 | 21.763 | — | — | — |
| fF | — | — | — | 121.000 | 133.00 | 139.150 |
| LZ | — | — | — | 164.506 | 164.506 | 164.506 |
| fR | — | — | — | 72.024 | 100.833 | 121.00 |
| fm | — | — | — | 39.690 | 31.185 | 22.779 |
| IH | — | — | — | 3.264 | 3.264 | 1.632 |

I claim:

1. A stereoscopic imaging optical system comprising, in order from its object side, one objective lens and a plurality of zoom imaging optical systems, characterized in that:
   each of said zoom imaging optical systems comprises, in order from its object side, a positive first group, a negative second group, an aperture stop, a positive third group and a positive fourth group, wherein:
   said second group moves on an optical axis for zooming,
   said fourth group moves on the optical axis in association with said second group for correcting an image position fluctuation incidental on zooming, and
   the following conditions are satisfied:

$$-1 < mg_{rw} < -0.2 \quad (1)$$

$$-0.4 < \Delta_{G4}/\Delta_{G2} < 0.4 \quad (2)$$

where $mg_{rw}$ is an imaging magnification at a low zoom ratio end of a whole of the groups on an image side with respect to the aperture stop,
   $\Delta_{G4}$ is a difference in an optical axis direction between a position of the fourth group at a low zoom ratio end and a position of the fourth group at a high zoom ratio end provided that + is on the image side, and
   $\Delta_{G2}$ is a difference in an optical axis direction between a position of the second group at a low zoom ratio end and a position of the second group at a high zoom ratio end provided that + is on the image side.

2. A stereoscopic imaging optical system comprising, in order from its object side, one objective lens, one afocal zoom optical system, one afocal relay optical system, a plurality of aperture stops, and a plurality of imaging optical systems, characterized in that:
   said afocal relay optical system comprises a front group and a rear group;
   there is an intermediate image between said front group and said rear group; and
   the following condition (3) is satisfied:

$$0.5 < f_F/L_Z < 0.9 \quad (3)$$

where $f_F$ is a focal length of the front group in the afocal relay optical system, and
   $L_Z$ is a maximum value of a distance from a surface located nearest to an object side to the surface located nearest to an image side of the afocal zoom optical system.

3. A stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following condition (4) is satisfied:

$$1.1 < f_F/f_R < 2 \qquad (4)$$

where $f_F$ is a focal length of the front group in the afocal relay optical system, and $f_R$ is a focal length of the rear group in the afocal relay optical system.

4. A stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following conditions (3) and (4) are satisfied:

$$0.5 < f_F/L_Z < 0.9 \qquad (3)$$

$$1.1 < f_F/f_R < 2 \qquad (4)$$

where $f_F$ is a focal length of the front group in the afocal relay optical system, $f_R$ is a focal length of the rear group in the afocal relay optical system, and $L_Z$ is a maximum value of a distance from a surface nearest to an object side to a surface nearest to an image side of the afocal zoom optical system.

5. A stereoscopic imaging optical system comprising, in order from its object side, one objective lens, one afocal zoom optical system, one afocal relay optical system, a plurality of aperture stops, and a plurality of imaging optical systems, characterized in that:

said afocal relay optical system comprises a front group and a rear group;

there is an intermediate image between said front group and said rear group; and the following conditions (3), (4) and (5) are satisfied:

$$0.5 < f_F/L_Z < 0.9 \qquad (3)$$

$$1.1 < f_F/f_R < 2 \qquad (4)$$

$$5 < fm/IH < 16 \qquad (5)$$

where $f_F$ is a focal length of the front group in the afocal relay optical system, $f_R$ is a focal length of the rear group in the afocal relay optical system, $L_Z$ is a maximum value of a distance from a surface nearest to an object side to a surface nearest to an image side of the afocal zoom optical system, fm is a focal length of each imaging optical system, and IH is a maximum image height on an imaging device located at an image position of the imaging optical system.

* * * * *